United States Patent
Friedrich et al.

(10) Patent No.: US 9,615,754 B2
(45) Date of Patent: Apr. 11, 2017

(54) INDUCING AND MEASURING MYOCARDIAL OXYGENATION CHANGES AS A MARKER FOR HEART DISEASE

(71) Applicant: CIRCLE CARDIOVASCULAR IMAGING INC., Calgary (CA)

(72) Inventors: Matthias Friedrich, Dorval (CA); Kady Fischer, Medicine Hat (CA); Jacqueline Flewitt, Calgary (CA); Dominik Günsch, Ittigen (CH)

(73) Assignee: Circle Cardiovascular Imaging Inc., Calgary (CA)

(*) Notice: Subject to any disclaimer, the term of this patent is extended or adjusted under 35 U.S.C. 154(b) by 71 days.

(21) Appl. No.: 14/419,877

(22) PCT Filed: Aug. 8, 2013

(86) PCT No.: PCT/CA2013/050608
§ 371 (c)(1),
(2) Date: Feb. 5, 2015

(87) PCT Pub. No.: WO2014/022935
PCT Pub. Date: Feb. 13, 2014

(65) Prior Publication Data
US 2015/0196207 A1 Jul. 16, 2015

Related U.S. Application Data

(60) Provisional application No. 61/680,981, filed on Aug. 8, 2012.

(51) Int. Cl.
*A61B 5/02* (2006.01)
*A61B 5/026* (2006.01)
(Continued)

(52) U.S. Cl.
CPC ........ *A61B 5/02028* (2013.01); *A61B 5/0075* (2013.01); *A61B 5/14542* (2013.01);
(Continued)

(58) Field of Classification Search
None
See application file for complete search history.

(56) References Cited

U.S. PATENT DOCUMENTS 7,747,308 B2 * 6/2010 Hundley .............. A61B 5/055
382/131
2013/0144140 A1 6/2013 Frederick et al.

FOREIGN PATENT DOCUMENTS

WO 2012/151583 A1 11/2012

OTHER PUBLICATIONS

Zheng, "Assessment of myocardial oxygenation with MRI", Quantitative Imaging in Medicine and Surgery, Apr. 2013, 3(2): pp. 67-72.
(Continued)

*Primary Examiner* — Brian T Gedeon
(74) *Attorney, Agent, or Firm* — Borden Ladner Gervais LLP; Kathleen E. Marsman

(57) ABSTRACT

The present disclosure relates to a method of assessing heart function and a system for assessing heart function. In detail, the present disclosure relates to a measuring a change in oxygenation or blood flow in the heart of the subject in response to a breathing maneuver and comparing the change in oxygenation or blood flow to a control. The change in oxygenation may be measured by segmenting an image of a heart, determining the signal intensity of a region of interest in a segment of the image and comparing the signal intensity to a control. An abnormal change in oxygenation blood flow or signal intensity in the heart compared to the control is indicative of reduced heart function. The disclosure further
(Continued)

relates to a system for diagnosing heart disease which comprises an imaging device and processor configured to assess heart function.

21 Claims, 17 Drawing Sheets

(51) Int. Cl.
    *A61B 5/029* (2006.01)
    *A61B 5/145* (2006.01)
    *A61B 5/00* (2006.01)
    *A61B 8/06* (2006.01)
    *A61B 8/08* (2006.01)
    *A61B 5/055* (2006.01)
    *A61B 5/053* (2006.01)
    *A61B 6/03* (2006.01)
    *A61B 6/00* (2006.01)

(52) U.S. Cl.
    CPC .............. *A61B 6/037* (2013.01); *A61B 6/503* (2013.01); *A61B 6/507* (2013.01); *A61B 6/5217* (2013.01); *A61B 6/5288* (2013.01); *A61B 8/065* (2013.01); *A61B 8/5223* (2013.01); *A61B 8/5284* (2013.01); *A61B 5/029* (2013.01); *A61B 5/053* (2013.01); *A61B 5/055* (2013.01); *A61B 6/032* (2013.01); *A61B 6/508* (2013.01)

(56) References Cited

OTHER PUBLICATIONS

Mason, "Non-invasive assessment of kidney oxygenation: a role for BOLD MRI", Kidney International, 70(1), Jul. 2006, pp. 10-11.
Arnold et al., "Myocardial Oxygenation in Coronary Artery Disease: Insights From Blood Oxygen Level-Dependent Magnetic Resonance Imaging at 3 Tesla", Journal of the American College of Cardiology, 59 (22), May 29, 2012, pp. 1954-1964.
Bauer et al., "Theory of Coherent and Incoherent Nuclear Spin Dephasing in the Heart", Physical Review Letters, 83 (20), Nov. 15, 1999, pp. 4215-4218.
Brown et al., "Exploiting Tumour Hypoxia in Cancer Treatment", Nature Reviews Cancer, Jun. 2004, vol. 4, pp. 437-447.
Christen et al., "Imaging Brain Oxygenation with MRI Using Blood Oxygenation Approaches: Methods, Validation, and Clinical Applications", AJNR Am J. Neuroradiol, Jun. 2013, pp. 1113-1123.
Dharmakumar et al., Detecting Microcirculatory Changes in Blood Oxygen State with Steady-state Free Precession Imaging, Magnetic Resonance in Medicine, 55 (6), published online May 5, 2006, publication dated Jun. 1, 2006, pp. 1372-1380.
Fieno et al., "Myocardial Perfusion Imaging Based on the Blood Oxygen Level-Dependent Effect Using T2-Prepared Steady-State Free-Precession Magnetic Resonance Imaging", Circulation, 110 (10), Sep. 7, 2004, pp. 1284-1290.
Friedrich et al., "Oxygenation-sensitive cardiovascular magnetic resonance", Journal of Cardiovascular Magnetic Resonance, 15 (43), May 24, 2013, pp. 1-11.
Friedrich et al., "Blood Oxygen Level-Dependent Magnetic Resonance Imaging in Patients with Stress-induced Angina", Circulation, 108 (18), Nov. 4, 2003, pp. 2219-2223.
Guensch et al., "Impact of Intermittent Apnea on Myocardial Tissue Oxygenation-A Study Using Oxygenation-Sensitive Cardiovascular Magnetic Resonance", PLOS ONE, vol. 8, issue 1, Jan. 3, 2013, pp. 1-6.
Guensch et al., "Non-invasive monitoring of blood gas-induced changes of myocardial oxygenation using oxygen-sensitive CMR", Journal of Cardiovascular Magnetic Resonance, 14(Suppl 1), Feb. 1, 2012, 2 pages.
Kelman, "Digital computer subroutine for the conversion of oxygen tension into saturation", Journal of applied physiology, 21 (4), Jul. 1966, pp. 1375-1376.
Manka et al., "BOLD cardiovascular magnetic resonance at 3.0 tesla in myocardial ischemia", Journal of Cardiovascular Magnetic Resonance, 12 (54), Sep. 22, 2010, pp. 1-9.
Morita et al., "Ischemic findings of T2* weighted 3-tesla MRI in acute stroke patients", Cerebrovasc Dis,. 26, Aug. 27, 2008, pp. 367-375.
Severinghaus, "Simple, Accurate Equations for Human Blood O2 Dissociation Computations", Journal of Applied Physiology, 46 (3), Mar. 1, 1979, pp. 599-602.
Shea et al., "T2-Prepared Steady-State Free Precession Blood Oxygen Level-Dependent MR Imaging of Myocardial Perfusion in a Dog Stenosis Model", Radiology, 236 (2), Aug. 1, 2005, pp. 503-509.
Tamura et al., Detection of Deoxygenation-Related Signal Change in Acute Ischemic Stroke Patients by T2*-Weighted Magnetic Resonance Imaging. Stroke, 33, 2002, downloaded Jan. 13, 2013, pp. 967-971.
Utz et al. "Blood Oxygen Level-Dependent MRI of Tissue Oxygenation: Relation to Endothelium-Dependent and Endothelium-Independent Blood Flow Changes", Arterioscler Thromb Vasc Biol., 25, accepted for publication Apr. 29, 2005, published 2005, pp. 1408-1413.
Varjavand et al., "The Interactive Oxyhemoglobin Dissociation Curve", www.ventworld.com/resources/oxydisso/dissoc.html, Jun. 1, 2000, 5 pages.
Vohringer et al. "Oxygenation-sensitive CMR for assessing vasodilator-induced changes of myocardial oxygenation", Journal of Cardiovascular Magnetic Resonance, Mar. 31, 2010, 12(20): pp. 1-7.
Wacker et al., "Changes in Myocardial Oxygenation and Perfusion Under Pharmacological Stress with Dipyridamole: Assessment Using T*2 and T1 Measurements", Magnetic Resonance in Medicine, 41 (4), Apr. 1999, pp. 686-695.
Weinsaft et al., "BOLD New Directions in Myocardial Ischemia Imaging-Myocardial Oxygenation Assessment by Cardiac Magnetic Resonance", The Journal of of the American College of Cardiology, 59(22), May 2012, pp. 1965-1967.
International Patent Application No. PCT/CA2013/050608, International Preliminary Report on Patentability, Feb. 10, 2015.
International Patent Application No. PCT/CA2013/050608, International Search Report and Written Opinion dated Oct. 1, 2013.
Kiviniemi et al., "Mapping Transient Hyperventilation Induced Alterations with Estimates of the Multi-scale Dynamics of BOLD Signal", Frontiers in Neuroinformatics, Jul. 15, 2009, vol. 3, Article 18, pp. 1-10.

* cited by examiner

INDUCING AND MEASURING MYOCARDIAL OXYGENATION CHANGES AS A MARKER FOR HEART DISEASE

CROSS REFERENCE TO RELATED APPLICATIONS

This application is a national phase entry of International Patent Application PCT/CA2013/050608 filed on Aug. 8, 2013, which claims the benefit of priority of U.S. Provisional Patent Application No. 61/680,981 filed on Aug. 8, 2012, which is hereby incorporated by reference.

FIELD

The present disclosure relates generally to methods and systems for assessing heart function. More particularly, the present disclosure relates to a method of using myocardial oxygenation or blood flow in association with a breathing maneuver to assess heart function.

BACKGROUND

Microvascular dysfunction is a hallmark of several diseases, including coronary artery disease (CAD or coronary atherosclerosis), most of them with high morbidity and mortality rates. Typically, blood supply and oxygen to the heart are affected, with consequences for longevity and quality of life. Furthermore, in the cascade of developing atherosclerosis, the deterioration of microvascular function is considered one of the first pathophysiological changes, occurring before any detectable morphological abnormalities. Thus, microvascular function is a target of choice for the early detection of atherosclerosis and other diseases affecting the heart such as diabetes, obesity, hypertension and hypercholesterolemia.

Currently, tests for coronary and microvascular function are performed using surrogate markers and physical or pharmacological stress (or vasodilatory) agents. Currently used techniques include electrocardiography (ECG), echocardiography, nuclear cardiology imaging (SPECT and PET), computed tomography (CT), and cardiovascular magnetic resonance (CMR). Surrogate markers are related to contractile function, tracer inflow or blood flow measurements. These are expected to indicate reduced macrovascular or microvascular function including the presence or absence of a significant coronary artery stenosis.

However, the use of physical or vasodilatory stress agents or exercise is contraindicated in some patients and pharmacological stress agents have potential dangerous and undesirable side effects and increase scan time and cost. Furthermore, for visualizing the inflow of blood, nuclear imaging uses a radioactive tracer, and CMR applies an intravenous bolus of an MRI contrast agent. This further impairs patient safety (injection, allergies, side effects) and increases scan preparation time and cost.

Myocardial oxygenation has also been used as a marker for ischemia and microvascular dysfunction. Oxygenation-sensitive CMR (OS-CMR) using the blood oxygen-level-dependent (BOLD) effect allows for non-invasive monitoring of changes in myocardial tissue oxygenation. OS-CMR detects changes in haemoglobin oxygenation by making use of the fact that its magnetic properties change when transitioning from oxygenated to deoxygenated status. While oxygenated haemoglobin (oxyHb) is diamagnetic exhibiting a weak stabilization of the magnetic field surrounding the molecule, de-oxygenated haemoglobin (de-oxyHb) is paramagnetic, de-stabilizing the surrounding field and thereby leading to a loss of magnetic field homogeneity, known as the BOLD effect. CMR protocols sensitive to the BOLD effect show a regional oxygenation-sensitive signal intensity (OS-SI or BOLD-SI) drop in tissues with such a relative increase of de-oxyHb, as seen in myocardial ischemia (Bauer et al. 1999; Wacker et al. 1999; Friedrich et al. 2003; Shea et al. 2005).

Several oxygenation-sensitive approaches have been used to detect coronary artery disease, using myocardial oxygenation changes in response to vasodilation by pharmacological agents such as adenosine or dipyridamole as a marker for myocardial ischemia (Friedrich et al. 2003; Fieno et al. 2004; Wacker et al. 1999; Bauer et al. 1999; Shea et al. 2005). While healthy vessels dilate and lead to an increase in myocardial signal intensity (SI), myocardium subtended by stenotic vessels show a blunted increase or a decrease in myocardial BOLD-SI in response to the vasodilatory trigger (Friedrich et al. 2003; Fieno et al. 2004; Wacker et al. 1999). However, these pharmacological agents have undesirable side effects such as bracycardia, arrhythmia, chest pain, bronchospasm, headache, nausea and heat waves. Furthermore, the injection of such vasoactive substances requires intravenous access and the availability of a medical doctor, additional cost for the vasodilatory agent, additional preparation time, and a risk for adverse events related to the injected agent.

Thus there remains a need for methods and systems for assessing the vascular integrity of the heart and diagnosing heart disease.

SUMMARY

Generally, the present disclosure provides a method for assessing the vascular function of the heart and a system for assessing heart function. In addition, disclosed herein is a method of diagnosing heart disease by assessing oxygenation of the heart, which is a reflection of the vascular integrity of the heart.

Disclosed herein is a method of assessing heart function or microvascular and/or macrovascular function in a subject. The method involves measuring a change oxygenation and/or blood flow in the heart or other organ of a subject in response to at least one breathing maneuver and comparing the change in the oxygenation and/or blood flow compared to a control. An abnormal response in the change in oxygenation and/or blood flow is indicative of reduced heart or microvascular and/or macrovascular function.

Also disclosed is a method of assessing heart function wherein the heart of a subject is imaged while the oxygenation of the heart is altered in response to at least one breathing maneuver. The resulting image is segmented and the signal intensity of a region of interest is compared to a control. An abnormal change in signal intensity compared to the control is indicative of reduced heart function.

The breathing maneuver may be a breath-hold or a period of hyperventilation and may be voluntary or induced by a machine. The control may be a baseline signal intensity which may be obtained prior to or at the start of the breathing maneuver. The control may also be a measured oxygenation or blood flow in a healthy tissue within the image or a measured oxygenation or blood flow in a stored image of a reference tissue. The reference tissue may be a healthy myocardium or other healthy organ or skeletal muscle.

The change in oxygenation may be measured using an oxygen sensitive imaging technique such as blood oxygen level dependent magnetic resonance imaging (BOLD-MRI), nuclear techniques, single-photon emission computed tomography/SPECT, positron emission tomography/PET, computed tomography/CT, echocardiography or other ultrasound, near infrared spectroscopy/NIRS, intravascular blood flow measurements, fractional flow reserve, or impedance measurements of the myocardium or other organ.

The methods disclosed herein may be used to assess microvascular or macrovascular function in the heart or other organ or to assess disease related to microvascular or macrovascular function such as heart disease or diseases of other organs. Heart disease may be ischemic heart disease, coronary heart disease, heart disease caused by arterial hypertension, diabetes mellitus, hypercholesterolemia, obesity, non-ischemic cardiomyopathies, or myocardial inflammation, congenital heart disease, valvular heart disease, stress-induced cardiomyopathy, microvascular dysfunction or coronary artery stenosis.

The methods disclosed herein do not include infusion of a vasodilator in the subject. An abnormal change may be a blunted increase compared to a control value, a lack of increase compared to a control, a decrease compared to a control or an increase compared to a control.

Also disclosed herein is a system for diagnosing heart or other organ function comprising
an imaging device and a processor configured to assess heart or other organ function according to the methods disclosed herein.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the attached Figures.

DETAILED DESCRIPTION

Generally, the present disclosure provides methods and a system for assessing heart function using non-invasive MR (or other) imaging. The degree and homogeneity of the response may serve as indicators of regional and/or global vascular function.

More particularly, the present disclosure relates to a method of assessing heart disease by measuring the distribution of oxygen and or blood flow in the heart in response to breathing maneuvers. Disclosed herein is a method of assessing heart function or microvascular/macrovascular function in a subject. An embodiment of the method involves measuring a change oxygenation and/or blood flow in the heart or other organ of the subject in response to at least one breathing maneuver and comparing the change in the oxygenation and/or blood flow compared to a control. An abnormal response in the change in oxygenation and/or blood flow is indicative of reduced heart or microvascular/macrovascular function.

Also disclosed is a method of assessing heart function wherein the heart of a subject is imaged while the oxygenation of the heart is altered in response to at least one breathing maneuver. The resulting image is segmented and the signal intensity of a region of interest is compared to a control. An abnormal change in signal intensity compared to the control is indicative of reduced heart function.

A system for diagnosing heart or other organ function is disclosed which comprises an imaging device and a processor configured to assess heart or other organ function according to the disclosed methods.

The methods disclosed herein are easy to perform and are relatively inexpensive. They allow for the measurement of changes in oxygenation and/or blood flow without the injection of vasodilators which are costly and induce unpleasant side effects. Furthermore, the methods disclosed herein are non-invasive and non-surgical and require very little preparation time in comparison to prior art methods that require the preparation of vasodilators for injection.

Figure 1:
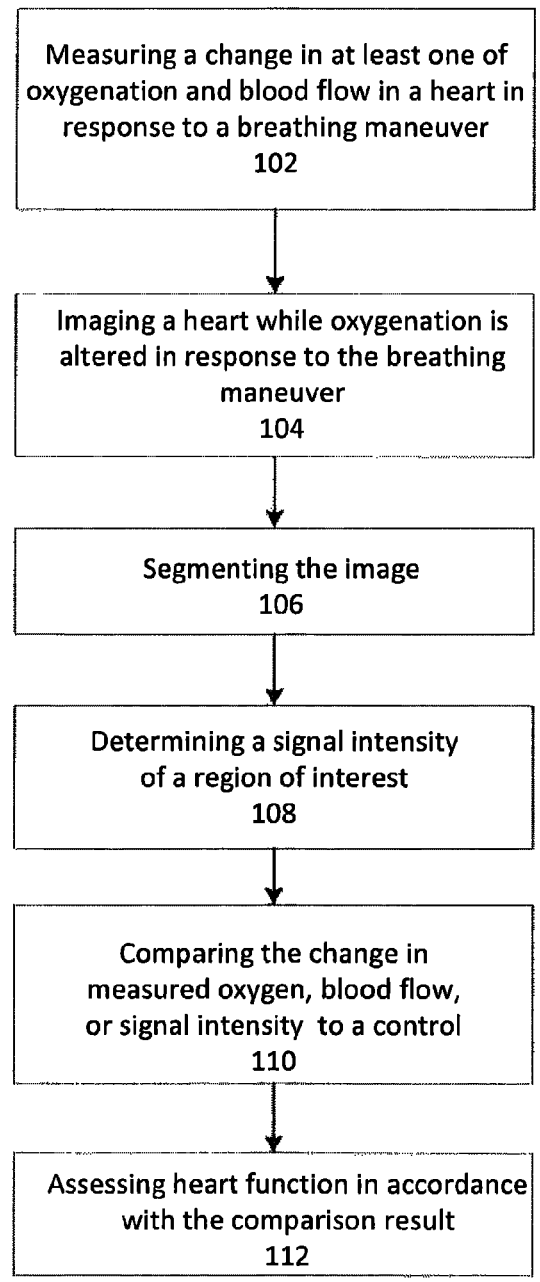
FIG. 1 is a flow chart outlining the method according to an embodiment.

FIG. 1 is a flow chart outlining the steps of a method disclosed herein. At step 102, a change in at least one of oxygenation and blood flow in a heart in response to a breathing maneuver is measured. The change in oxygenation may be measured by imaging the heart at step 104, segmenting the image at step 106 and determining a signal intensity of a region of interest at step 108. At step 110, the signal intensity determined at step 108 or the change in oxygenation or blood flow measured at step 102 is compared to a control. At step 112 heart function is assessed in accordance with the comparison result, wherein an abnormal change in oxygenation or blood flow in the heart compared to the control is indicative of reduced heart function.

As used herein, the term "heart function" is meant to include vascular function, for example, microvascular or macrovascular function. A diseased heart may show reduced function compared to a normal heart, whereas an athlete's heart may show increased function relative to a normal heart. The methods disclosed herein may be used to assess decreased or increased heart function relative to a normal or control heart.

As used herein, the term "heart disease" is meant to include any disease relating to the heart. These include but are not limited to ischemic heart disease or heart disease caused by arterial hypertension, diabetes mellitus, hypercholesterolemia, obesity, non-ischemic cardiomyopathies, myocardial inflammation, congenital heart disease, valvular heart disease, stress-induced cardiomyopathy, or infiltrative myocardial disorders. The disease may be microvascular disease (for example in hypertension, diabetes, sleep apnea, hypercholesterolemia, "syndrome X", immunologic and rheumatologic diseases) or macrovascular (stenotic coronary artery disease) disorders. Additional examples of heart disease include but are not limited to cardiomegaly, and stress-induced angina.

"Assessing" heart disease or heart function includes but is not limited to diagnosing heart disease, predicting the risk of developing heart disease, and monitoring the progression of heart disease. For example, assessing includes diagnosing heart disease in subjects with chest pain of unknown origin, or for diagnosing subjects with atypical symptoms consistent with coronary atherosclerosis. The method may also be used to assess whether a subject is at risk of developing heart disease (i.e. a large-scale population wide screening for cardiovascular risk) or assessing whether the disease has initiated or developed in a subject at risk of developing heart disease. Therefore, "assessing" is meant to include predicting risk for developing heart disease and risk stratification of subjects. This includes predicting the risk of developing hypertension, hypercholesterolemia, diabetes or other systemic disease, which may affect microvascular or microvascular function in the myocardium. Assessment may include assessing the severity of coronary artery stenosis in patients with known coronary artery disease. Assessing may include monitoring disease progression in individuals diagnosed with heart disease. This may include subjects receiving treatment or subjects who are not receiving treatment. For example, assessing includes evaluating the impact of therapeutic interventions such as medications, exercise programs or the like on the established heart disease, and in particular, microvascular function and oxygenation.

Assessing heart disease may also include determining whether significant coronary artery stenoses are present in the preoperative workup of subjects scheduled for surgery or during interventional revascularization in coronary artery disease. In addition the term "assessing heart disease" is meant to include the assessment of the impact of non-ischemic cardiovascular disease (e.g. infiltrative or inflammatory myocardial disease) on microvascular function and oxygenation or for assessment of the impact of systemic diseases (e.g. viral infection) on microvascular function and oxygenation. It is also possible to use the methods described herein to stratify or "assess" the risk of developing heart disease for family members considered at increased risk for coronary atherosclerosis.

"Assessing" heart function may include testing for healthy subjects and monitoring cardiovascular health over time, or monitoring a change in heart function in response to an exercise program or change in lifestyle, which may include changes in exercise or changes to food and fluid intake.

The term "risk factors" is meant to include any factor that results in a predisposition to heart disease and would be known to a person of skill in the art. Risk factors related to heart disease such as coronary atherosclerosis include but are not limited to hypertension, diabetes, obesity, age, sex, genetic disposition, smoking, or previous heart disease. Risk factors may also include but are not limited to iatrogenic factors (e.g. secondary to radiation therapy), infection, inflammation, and neoplasm.

As used herein a "subject" refers to any human or animal that would benefit from the assessment of heart function. Non-limiting examples of a subject include humans, non-human mammals, companion mammals, livestock and the like. A subject can further be a healthy human or animal that will provide useful information to understanding and diagnosing heart disease or further improving the protocol or technical specifications of OS-CMR.

A subject at risk may be a subject that does not show any signs of having heart disease; a subject that shows signs of the disease but has not yet been diagnosed; a subject that has been diagnosed but has not undergone treatment; a subject that has undergone treatment.

The term "breathing maneuvers" is meant to include any alteration to the natural, unconscious control of breathing. Unconscious control of breathing is mediated by specialized centers in the brainstem which automatically regulate the rate and depth of breathing. Thus, breathing maneuvers may include, for example, a change in the rate or the depth of the breath. Breath-holds and hyperventilation are examples of breathing maneuvers. Breathing maneuvers may be voluntary (i.e. in response to conscious control of breathing) or induced mechanically. Certain embodiments use multiple breathing maneuvers or combinations of breathing maneuvers.

As used herein the term "breath-hold" is used interchangeably with "apnea" and refers to the suspension of breathing. The term "hyperventilation" defines a breathing rate that is faster than the momentary resting breathing rate of the subject or a breathing rate faster than the rate required to maintain physiologic $paCO_2$ levels (40+/−5 mmHg) for ventilated subjects. The suspension of breathing may be induced mechanically through manipulation of specialized devices (e.g. ventilation bag) or machines such as a ventilator or may be induced naturally and voluntarily without the use of an external machine. In patients with other pre-existing diseases (e.g. pulmonary diseases) the $paCO_2$ levels may be different from those naturally defined as physiologic. A person of skill in the art would be able to define the appropriate baseline $pCO_2$ levels and baseline respiratory rate for those subjects. Specialized machines may allow for a fine-tuned change of blood carbon dioxide and/or oxygen using simultaneous blood gas analysis and feedback mechanisms to regulate the inhaled gas composition. An example of a suitable machine for regulating inhaled gas composition is a Harvard ventilator, but other machines would be known to a person skilled in the art. In one embodiment, breath-holds may be achieved in an anaesthetized ventilated model. In another embodiment standardized voluntary breathing maneuvers were used.

Breath-holds may be from 5 seconds to 3 minutes in length. In a preferred embodiment a breath-hold is about 1 minute. A breath-hold may be 5 seconds, 10 seconds, 15 seconds, 20 seconds, 25 seconds, 30 seconds, 35 seconds, 40 seconds, 45 seconds, 50 seconds, 55 seconds, 60 seconds, 65 seconds, 70 seconds, 75 seconds, 80 seconds, 85 seconds, 90 seconds, 95 seconds, 100 seconds, 105 seconds, 110 seconds, 115 seconds, 120 seconds, 125 seconds, 130 seconds, 135 seconds, 140 seconds, 145 seconds, 150 seconds, 155 seconds, 160 seconds, 165 seconds, 170 seconds, 175 seconds or 180 seconds. A breath-hold may also be maximal. By maximal it is intended to mean the maximum length of time a subject may voluntarily hold their breath. Multiple breath-holds may be used in the methods described herein.

In an embodiment the methods are performed using standardized breathing maneuvers. For example, the breathing maneuver may be a period of hyperventilation. The methods may include multiple periods of hyperventilation or breath-holding or a combination of periods of hyperventilation and breath-holding. For example, three minutes of hyperventilation, followed by 30 seconds of breath-holding may be used in the methods disclosed herein.

In an embodiment, the $pCO_2$ (arterial, peripheral or end-tidal) and $pO_2$ (arterial, peripheral, inspiratory or expiratory gas concentrations) or $SpO_2$ are adjusted to a baseline level of a target e.g. $paO_2$ of 100 mmHg and a target $paCO_2$ of 40 mmHg, $SpO_2$ of 95-98%.

Changes in oxygenation or blood flow induced by breathing maneuvers may be measured using any diagnostic technique capable of detecting regional or global variations of myocardial perfusion or oxygenation. Examples include but are not limited to oxygenation-sensitive CMR, nuclear cardiology techniques (single-photon emission computed tomography/SPECT, positron emission tomography/PET, computed tomography/CT, echocardiography, near infrared spectroscopy/NIRS intravascular blood flow measurements such as fractional flow reserve, or impedance measurements of the myocardium. In an embodiment, T2* weighted steady-state-free-precession (SSFP) protocols in a 1.5 T MRI system were used. In a further embodiment, a 3.0 T MRI system was used. Appropriate diagnostic techniques would be known to a person of skill in the art.

In an embodiment the method comprises inducing a breath-hold in a subject; measuring the change in oxygenation-sensitive magnetic resonance signal intensity or T2* in the heart of the subject during breathing maneuvers; and assessing heart disease, wherein heart disease is indicated by an abnormal response, typically a lack of increase or even decrease in iOS-CMR signal intensity or T2* in oxygenation-sensitive images compared to a control. The image of the subject may be obtained by OS-CMR and segmented according to procedures that are known to a person skilled in the art. Segments of the heart may then be compared and myocardial segments that are subtended by vessels with stenosis may be identified as regions with decreased signal intensity or T2* relative to other segments, which represent normal tissue. In one embodiment the control is a myocardial segment within the heart that is "normal" and does not show evidence of an abnormal response which would indicate abnormal microvascular function or stenosis of a related coronary artery.

The control may be an image obtained by OS-CMR, or signal intensity ranges or T2* that have been previously obtained from a subject with a normal (or non-diseased) heart. The control may also be data or images that relate to blood flow in a normal heart or reference organ. The image or data may have been previously stored in a database. In an embodiment the signal intensities of the subject are compared to the signal intensities or T2* obtained from the stored image. The stored control images may be categorized according to age, sex, type of disease, for example, and a control may be "matched" to the subject. The control tissue may further be healthy myocardium within the same scan from the same subject that shows OS-SI changes in an expected manner which pre-defines healthy myocardium, it may be myocardium where the normal SI is exhibited by normalization with reference tissue (e.g. skeletal muscle) or it may be the reference tissue itself that is compared to segments suspected of cardiac disease.

Baseline SI or T2* (at a resting state) BOLD images may be obtained in or on one or several standardized short and/or long axis slices. OS-SI or T2* during or after a breathing maneuver may be compared to the baseline values. During breath-holds, continuous image acquisitions are possible. In hyperventilation maneuvers images may be acquired after the breathing maneuvers in a short breath-hold. Images can also be obtained during free breathing in navigator monitored or gated free breathing sequences. In these sequences SI or T2* changes can be compared during changes of respiratory rate (e.g. changing from the normal baseline respiratory rate to hyperventilation (respiratory rate 20-40/min)) which may also include breath-holding (respiratory rate=0/min). Breath-holding will lead to an increase in $pCO_2$ and thus lead to an increase in blood flow and myocardial oxygenation in healthy myocardial tissue that can be measured with OS-CMR. Hyperventilation will result in the opposite. Myocardium with microvascular dysfunction is expected to show a different behaviour in OS-CMR as compared to healthy myocardium to breathing maneuver challenges. Signal intensity or T2* evolution can be analyzed by comparing baseline values to the mean or maximal deflection (maximal/minimal SI/T2* changes) at specific time points during or at the end of the maneuver or the signal evolution over time. In the latter case the slope of the SI/T2* change (% change SI/s) may be indicative of healthy or diseased myocardium.

Myocardial borders may be manually traced by the reader or automatically by evaluation software. The myocardium may be assessed based on defined segments, e.g. the "AHA segmentation model". The SI or T2* changes may be compared to the control or baseline images or signals in a database or other myocardial segments. The increase/decrease (absolute SI or T2* changes, changes in % from the control or baseline, SI/T2* changes over time, maximal or minimal SI or T2*) in BOLD-SI or T2* images would be deemed normal or pathologic. The T2* mapping technique defines a diagnostic threshold value of which myocardial segments are deemed healthy or diseased. In such a case breathing maneuver images may not need to be compared to baseline images.

The administration of adenosine in patients with severe coronary artery stenosis is currently used in clinical applications and leads to either a blunted increase, a lack of increase or a decrease of myocardial oxygenation in related myocardial regions compared to a normal control (Luu et al., in preparation; Friedrich et al., 2003). In these studies, BOLD MRI was used to detect myocardial ischemia related to severe coronary stenoses in patients with stress-induced angina. Since the change in signal intensity in normal tissue using breathing maneuvers is improved relative to those seen using adenosine, it follows that the instant methods may be used to assess heart disease and heart function.

The threshold value for observed changes of myocardial oxygenation may change in response to subject-related factors such as age, gender, level of physical fitness, and the disorder to be assessed as well as technical conditions related to altitude and technology used for measurement (MR field strength, nuclear cardiology tracers, flow probes). Cutoff values related to an increase of myocardial blood flow by a minimum of 100% or an increase of the OS-MR signal intensity of a minimum of 3% may be used as an indicator of a preserved response. Similarly, a decrease in change in OS-MR signal intensity of 3% relative to a control may be sufficient to discriminate diseased heart (or reduced heart function) from normal heart. These values will also be subject to the precise breathing maneuver protocol, the field strength and the used MR protocol ("sequence").

The method disclosed herein may be used to assess ischemic heart disease or heart disease caused by arterial hypertension, diabetes mellitus, hypercholesterolemia, or obesity, non-ischemic cardiomyopathies, myocardial inflammation, congenital heart disease, valvular heart disease, stress-induced cardiomyopathy, or infiltrative myocardial disorders. The disease may be microvascular disease (for example in hypertension, diabetes, sleep apnea, hypercholesterolemia, "syndrome X", immunologic and rheumatologic diseases) or macrovascular (stenotic coronary artery disease) disorders. The methods may also be used to assess the function of a normal heart.

Disclosed herein is a system that uses changes of oxygenation in the heart muscle or blood flow as a marker for heart disease or involvement of the heart in systemic disease by combining an imaging device or a device to measure blood flow, e.g. an MRI scanner, with a processor configured to assess heart function. The processor is a programmable processor such as a microprocessor. The system allows for measurement of the response of the oxygen metabolism or blood flow in the heart muscle and using the resulting changes of myocardial oxygen or blood flow as a marker for assessing heart function, including but not limited to the diagnosis of microvascular and macrovascular disease. A normal response is closely linked to a healthy microvascular environment. An abnormal response may be used as a diagnostic marker for diseases of the small vessels. The system may be offered as a specific combination of an MRI scanner with a device to alter breathing patterns.

The method or system may be used in hospitals, clinics or private practices. In an embodiment, the method or system may be combined with blood tests and genomic analysis to allow for a comprehensive stratification or classification of the atherosclerotic risk of a subject. In another embodiment, the method or system may comprise a combination of devices to modify blood gases along with breath-holds and MRI of the heart for diagnostic purposes or to assess heart function.

The method or system may also be used to assess the microvascular response in the brain, kidneys or other organs. Indeed, BOLD imaging has been used for many years in the field of cognitive neuroscience. Both, simple $T2^*$ estimates of oxygenation and more advanced quantitative BOLD techniques have been used to detect oxygenation changes in different brain disorders. $T2^*$ measurements have been proposed to delineate the penumbra in acute stroke (Tamura et al., 2002; Morita et al., 2008). Furthermore, BOLD imaging has the potential to assess oxygenation status of brain tumours (Brown and Wilson, 2004). Many other brain disorders such as Alzheimer disease, Parkinson disease and Huntington disease have been associated with alterations in cerebral oxygenation metabolism (Christen et al., 2012). Oxygenation-sensitive CMR has also been applied to assess endothelial function in skeletal muscle (Utz et al., 2005) and oxygenation of kidneys (Mason, 2006). Thus, the methods disclosed herein that result in changes in oxygen sensitive CMR may be used to assess these diseases.

To gain a better understanding of the invention described herein, the following examples are set forth. It should be understood that these examples are for illustrative purposes only. Therefore, they should not limit the scope of the invention in any way.

Example 1

An Anaesthetized Ventilated Porcine Model to Assess Changes in Myocardial Oxygenation Due to Controlled Apnea at Physiologic Baseline Levels Methods
Animal Preparation Protocol Nine juvenile male pigs (24.3±0.2 kg) were pre-medicated with 600 mg Ketamine, 10 mg Midazolam and 2 mg Fentanyl i.m., then anaesthetized with 20-25 mg/kg Thiopental to establish an appropriate anaesthesia depth. They were intubated with a standard cuffed endotracheal tube (ID 5.5-6 mm) and ventilated with a Harvard Ventilator. Anaesthesia was maintained with an intravenous drip (1-3 mg/h Midazolam, 1.6-4.8 mg/h Fentanyl) and a nitrous oxide/Isoflurane (0.6-1.5%) gas narcosis. To prevent arrhythmia, the animals received a continuous Lidocaine infusion (1 mg/min). The right carotid artery and the femoral artery were cannulated for invasive blood pressure and arterial blood gas measurements throughout the experiment. The left jugular and femoral vein were cannulated for intravenous infusions. Monitoring of anaesthesia and haemodynamics included $EtCO_2$, $FiO_2/FiN2O$, 3-lead ECG, invasive blood pressure and arterial blood gases.

MRI Imaging Protocol

After preparation, the animals were transferred to a clinical 1.5 T MRI system (Avanto™, Siemens Healthcare, Erlangen, Germany). Custom 12 m long ventilator tubing connected the ventilator from outside the MR suite. Blood gases were adjusted to a target $paO_2$ of 100 mmHg and a $paCO_2$ of 40 mmHg. Then, BOLD-sensitive steady-state-free-precession (SSFP) cine images were acquired in mid left-ventricular short axis views (slice thickness 10 mm, TE 2.78 ms, TR 5.56 ms, flip angle 90°, FOV variable, matrix 128×72). Each cine loop was composed of 20 phases covering the entire cardiac cycle, obtained by retrospective ECG gating. BOLD-SSFP cines were acquired during a 1 min breath-hold. Breath-holds were induced by switching off the ventilator. Immediately after resuming ventilation an arterial blood sample was taken to determine the changes in blood gas levels over the one minute breath-hold. Blood gases were utilized to calculate the approximate arterial haemoglobin saturation using a dissociation curve tool (Varjavand 2000) based on the equations of Kelman and Severinghaus (Kelman 1966; Severinghaus 1979).

Image Analysis

The images were analyzed using certified software for CMR image analysis (cmr[42], Circle Cardiovascular Imaging Inc., Calgary, AB, Canada). Image quality was graded prior to SI measurement using visual assessment based on a 1-4 scale: 1=good image quality, 2=mildly impaired image quality resulting in <10% of the total myocardial area excluded, 3=limited image quality resulting in >10% of the myocardium excluded, 4=a severely non-analyzable image. The mean myocardial SI in the BOLD-sensitive images was automatically calculated after manual tracing of endocardial and epicardial contours in all images of each cine series. Additionally, a region of interest was defined in the centre of the left ventricular (LV) lumen for assessing SI changes in the arterial blood during the breath-hold.

Figure 2:
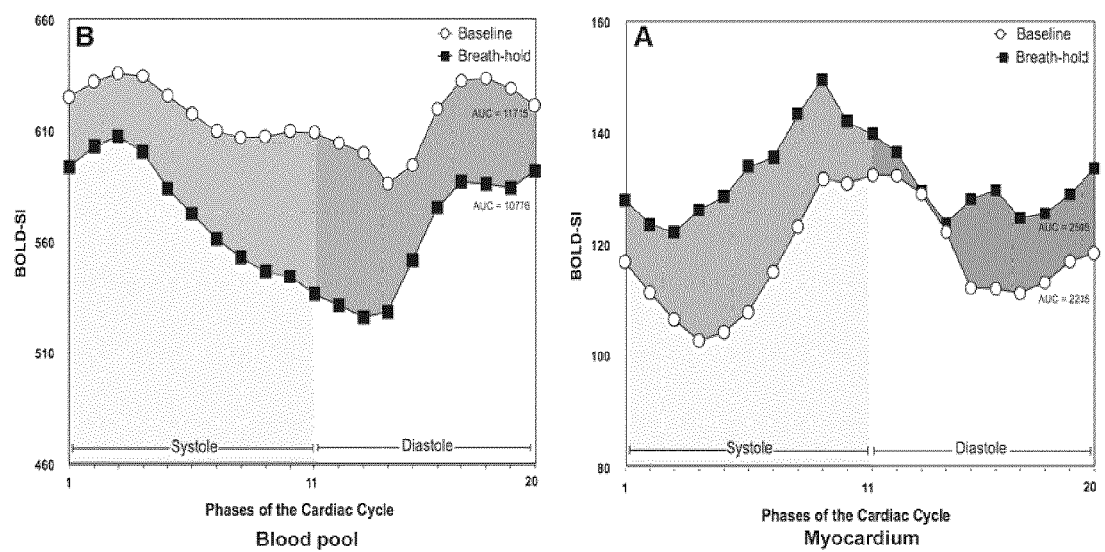
FIG. 2 shows OS-SI in CMR analysis of 20 phases of a cardiac cycle in swine before and after a 60 s breath-hold.

FIG. 2 shows OS-SI in CMR analysis of 20 phases of a cardiac cycle before and after a 60 s breath-hold. For the entire cardiac cycle, the area under the curve (AUC) was calculated from the signal intensity of all 20 phases and expressed as percent change SI between baseline and the end of the breath-hold.

Statistical Analysis

To determine the SI changes resulting from apnea, the AUC of the first two image sequences were compared to those of the last two images of the breath-hold using a paired t-test. Additionally, differences in blood gases and cardiovascular parameters over the breath-hold were analyzed with a paired t-test. Pearson's correlation was performed to determine if there were relationships between the %-change SI and changes in blood gases, heart rate and blood pressure. Values are expressed as mean±SEM. Statistical analysis was calculated with GraphPad Prism (GraphPad Software, San Diego, Calif.) and deemed significant if $p \leq 0.05$.

Results

One pig was excluded due to a pre-existing severe myocardial wall motion abnormality at baseline. Two pigs died in a sudden cardiac arrest during the preparation of the blood vessels, leaving 6 pigs for the data analysis. Overall, BOLD image quality was good in this study as visual assessment yielded a mean score of 1.3±0.3. One pig had 10%-15% of the myocardium excluded in the anterolateral and inferolateral segments due to susceptibility artifacts and two other pigs had, 10% exclusions in the inferoseptal, inferior and inferolateral segments.

Blood Gases and Cardiovascular Parameters

The $paCO_2$ significantly increased from 41±0.4 to 47±1 mmHg during apnea (p<0.001) accompanied by a significant decrease in pH from 7.40±0.02 to 7.35±0.01 (p=0.009) as shown in Table 1. Also, there was a significant decrease in $paO_2$ from 100±2 to 65±5 mmHg (p=0.003). As a result of the changing $paO_2$, $paCO_2$ and pH levels, the calculated $SaO_2$ dropped by 9.9±3.5% (p=0.037). There was no change in heart rate but all animals, however, showed a significant drop in blood pressures (p<0.05).

TABLE 1

Changes of arterial blood gases, blood pressure and heart rate in swine before and after a 60 second breath-hold.

|  | Baseline (n = 6) | After Apnea (n = 6) | p Value |
|---|---|---|---|
| Arterial blood gates [mmHg] |  |  |  |
| $paCO_2$ | 41 ± 0.4 | 47 ± 1 | <0.001 |
| $paO_2$ | 100 ± 2 | 65 ± 5 | 0.003 |
| pH | 7.40 ± 0.02 | 7.35 ± 0.01 | 0.009 |
| Arterial blood pressures [mmHg] |  |  |  |
| Systolic | 100 ± 11 | 85 ± 18 | 0.013 |
| Mean | 74 ± 9 | 64 ± 13 | 0.035 |
| Diastolic | 59 ± 9 | 50 ± 11 | 0.029 |
| Heart rate [beats/min] | 110 ± 14 | 114 ± 14 | 0.448 |

Mean (±SEM) arterial partial pressures (mmHg) of blood gases, invasive blood pressures from the femoral artery and heart rate (n ± 6).
doi:10.1371/journal.pone.0053282.t001

CMR Results

Figure 3:
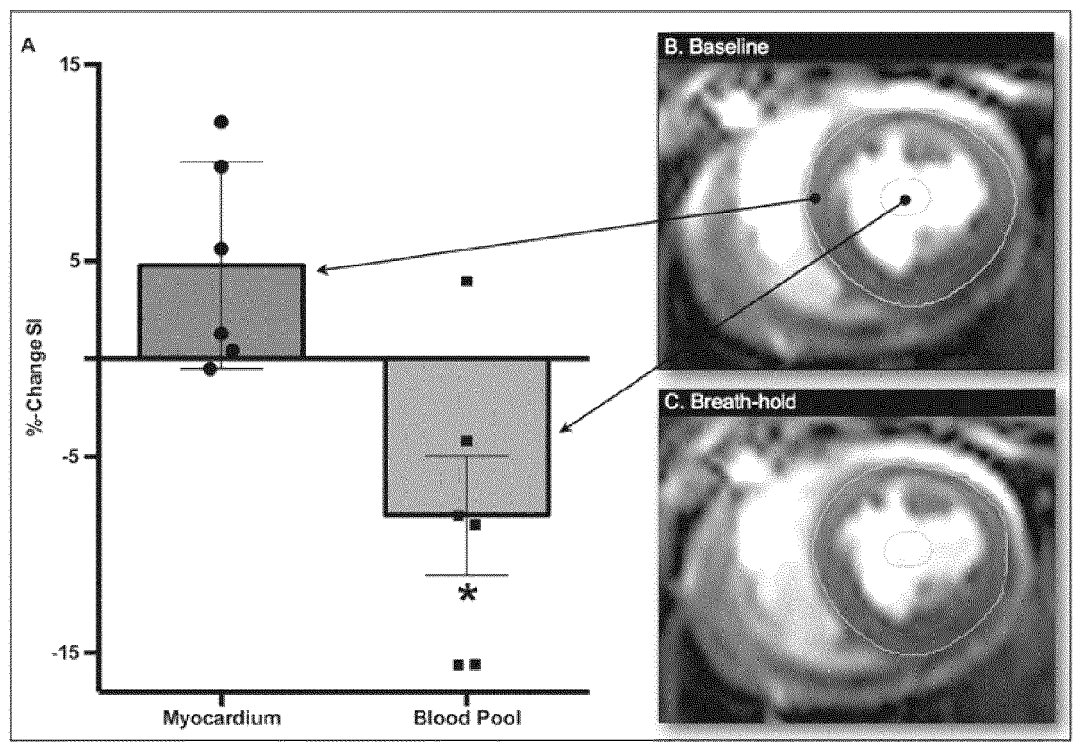
FIG. 3 shows OS-CMR analysis of the myocardium and the left ventricular blood pool during a 60 s breath-hold in swine.

FIG. 3 shows OS-CMR analysis of the myocardium and the left ventricular blood pool during a 60 s breath-hold in swine. Between 6 and 8 BOLD SSFP cine series were acquired during the apneic periods. During apnea, there was a strong, yet non-significant trend for an increase of myocardial SI (4.8±2.2%; p=0.077).

Figure 4:
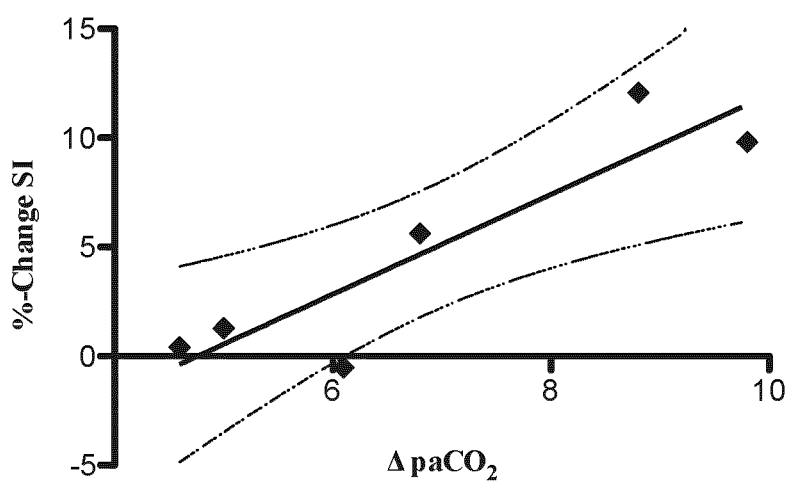
FIG. 4 shows the difference in $paCO_2$ (mmHg) plotted against the %-change in myocardial SI (n=6) in swine.

FIG. 4 shows that that the increase in myocardial SI was linearly correlated with the change in $paCO_2$ (r=0.90, p=0.010) while there was no correlation between myocardial SI changes and changes of $paO_2$. SI in the LV blood pool decreased during apnea by 8.0±3.0% (p=0.047). The relative drop in blood pool SI detected by oxygenation-sensitive MR was similar to the 9.9±3.5% (p=0.037) drop in calculated $SaO_2$. Heart rate was not correlated with changes in SI.

Example 2

An Anaesthetized Ventilated Porcine Model to Assess Changes in Myocardial Oxygenation Due to Controlled Apnea from a Wider Range of Baseline $paCO_2$ and $paO_2$ Levels Methods Anaesthesia and Animal Protocol Nine juvenile male pigs (24.3±0.2 kg) were used for this study. The anesthesia and animal preparation was identical to that explained in part A.

Experimental Protocol

Figure 5:
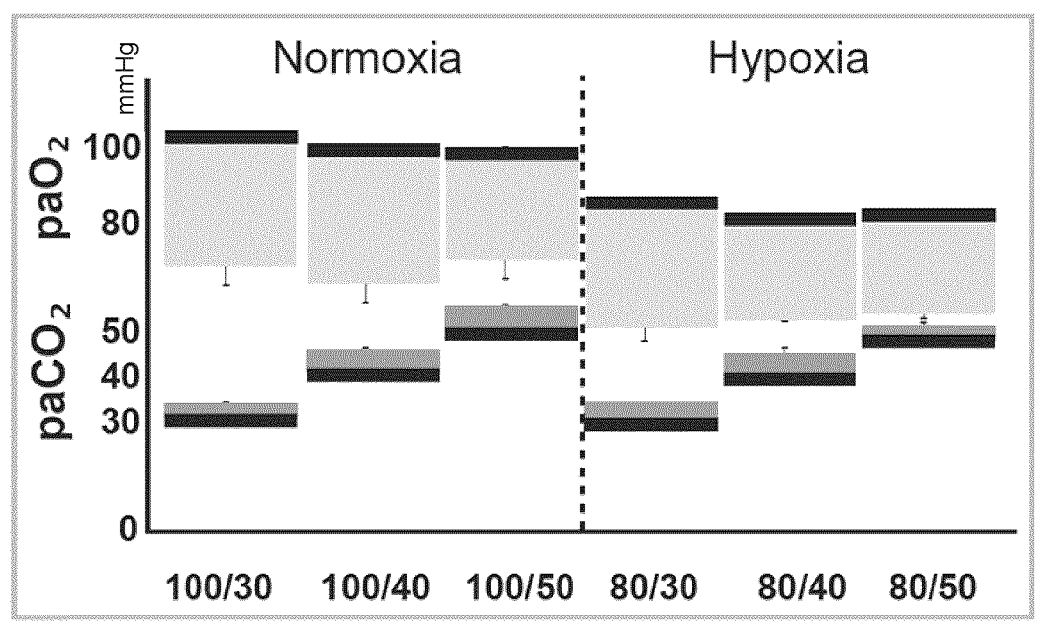
FIG. 5 shows target baseline $paO_2/paCO_2$ levels and blood gas changes during a 60 s breath-hold in swine.

FIG. 5 shows a range of $paO_2/paCO_2$ levels that were used as a target baseline and blood gas changes that occurred during a 60 s breath-hold in swine. Six baseline blood gas levels were targeted ($paO_2$: 100 and 80 mmHg; $paCO_2$: 30, 40 and 50 mmHg) by modulating the ratio of inspiratory $O_2/N_2O$ gas fraction and the ventilation rate. This way hypocapnia and hypercapnia were assessed in combination with normoxemia or hypoxemia in addition to a normal blood gas level previously published (Guensch et al. 2012). Once a level was attained, a 60 s breath-hold was induced by pausing ventilation at end-expiration. Immediately after resuming ventilation, a second arterial blood sample was taken to determine the changes in blood gas levels over the breath-hold. Blood gases were utilized to calculate the approximate arterial hemoglobin saturation using a dissociation curve tool (Varjavand 2000) based on the equations of Kelman (Kelman 1966) and Severinghaus (Severinghaus 1979).

CMR Imaging Protocol

All imaging was performed in a clinical 1.5 T MRI system using a body matrix coil (Avanto®, Siemens Healthcare, Erlangen, Germany). Single slice BOLD-sensitive steady-state-free-precession (SSFP) cine images were acquired continuously throughout a 60 s breath-hold of the mid left-ventricular short axis (Slice Thickness 10 mm, Echo Time 2.78 ms, Repetition Time 44.48 ms, Flip Angle 90°, Field of View 280×157.5, matrix 128×72). Each cine series was composed of 20 phases covering the entire cardiac cycle, obtained by retrospective ECG gating.

Image Analysis

Mean SI of the left ventricular (LV) myocardium and arterial blood was obtained from images using certified software for CMR image analysis (cmr[42], Circle Cardiovascular Imaging Inc., Calgary, AB, Canada). Myocardial SI was defined by the manual tracing of endocardial and epicardial contours, and the arterial blood by a region of interest in the LV lumen. For each cine, the area under the curve (AUC) was calculated from the signal intensity of all 20 phases to provide a single value for each acquisition. The SI from the first two cines of the breath-hold were compared to the final two cines and expressed as percent change SI measured across a 60 s breath-hold. The % change in SI is reported for both the myocardium (MyoSI) and the left ventricular blood pool (LVbpSI). To compensate for the two competing effects of arterial desaturation and increase in $CO_2$-mediated blood flow, the difference between LV-blood pool SI change and myocardial SI change is reported as calculated SI change ($SI_{calc}$). This myocardial SI corrected for desaturation calculates as $SI_{calc}$=MyoSI(%)−LVbpSI (%).

Statistical Analysis

Changes in values at baseline and after a breath-hold were compared using paired t-tests. Changes in SI of both the myocardium and blood pool were compared to the changes in $paCO_2$, $paO_2$, heart rate (HR), mean arterial blood pressure (MAP) and calculated $SaO_2$ with linear correlation and multiple regression analysis. Statistical analysis was considered significant if *P<0.05.

Results

For each level there were 6 successful subjects due to two premature deaths and one to a pre-existing cardiac abnormality. All images were of sufficient image quality and none were excluded.

Image Quality

Figure 6:
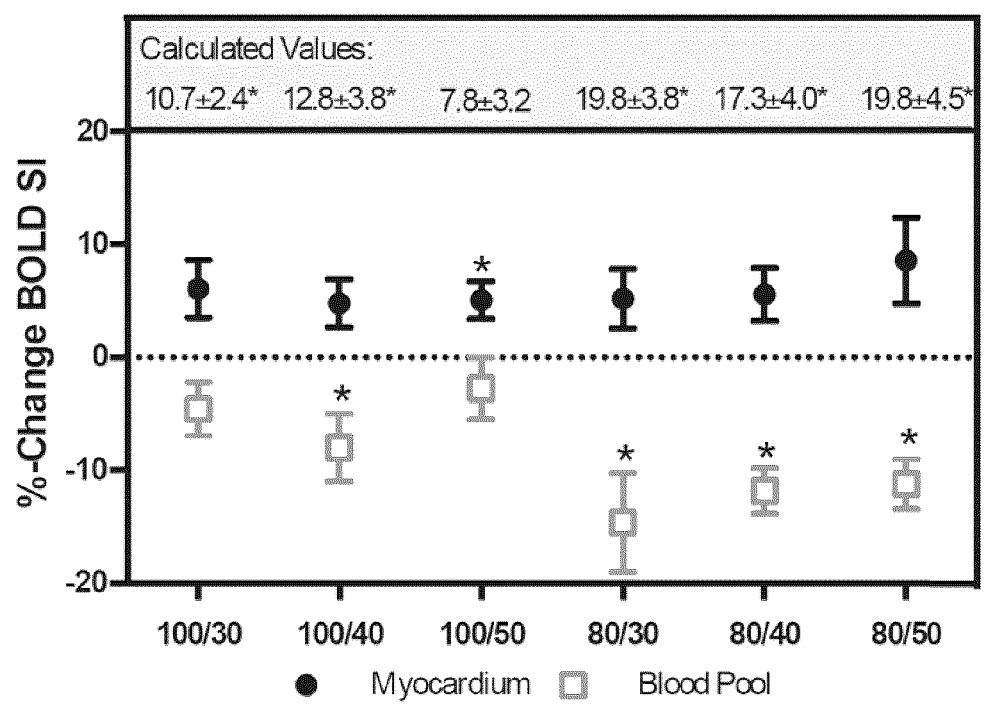
FIG. 6 shows mean % change+/−SEM in OS-SI during a 60 s breath-hold in swine at multiple baseline blood gas levels in the myocardium and the left ventricular blood pool, as well as the myocardial SI corrected for left ventricular desaturation in swine.

FIG. 6 shows mean % change+/−SEM in OS-SI during a 60 s breath-hold from several baseline blood gas levels in the myocardium, the left ventricular blood pool as well as the myocardial SI corrected for left ventricular desaturation. The initial baseline SI did not differ between the different levels and the %-change SI is the reported value. The MyoSI showed a similar trend of increasing SI of at least 5.2% for each level (FIG. 6). On the other hand the LVbpSI decreased, but the degree of change differed between some levels. The decrease was not as pronounced in the normoxemic levels ($paO_2$ 100 mmHg), yet a larger and significant drop of at least 11% (*P<0.02) was observed in the hypoxemic levels ($paO_2$ 80 mmHg). The same effect was seen in the $SaO_2$ calculation. There was an increase in the calculated myocardial SI of at least 17% in the hypoxic levels (*P<0.01) and at least 10% for the levels 100/30 and 100/40 (*P<0.05), with 100/50 to be the only level with a non-significant increase (+7.8%, P=0.08).

Blood Gas Analysis $PaCO_2$ and $paO_2$ levels were analyzed for all blood samples (n=6) except for the post breath-hold oxygen tension from 1 animal of the 80/40 level resulting in n=5. Analysis of the arterial blood samples (FIG. 5) from each level showed that $paCO_2$ increased significantly while the oxygen partial pressures all decreased by a minimum of 25 mmHg after a 60 s breath-hold. These changes were consistent among all the levels. Like the changes in LVbpSI, there was a greater decrease in calculated $SaO_2$ in the hypoxemic levels compared to the normoxemic levels.

Relationship of Signal Intensity to Blood Gas Levels

Figure 7:
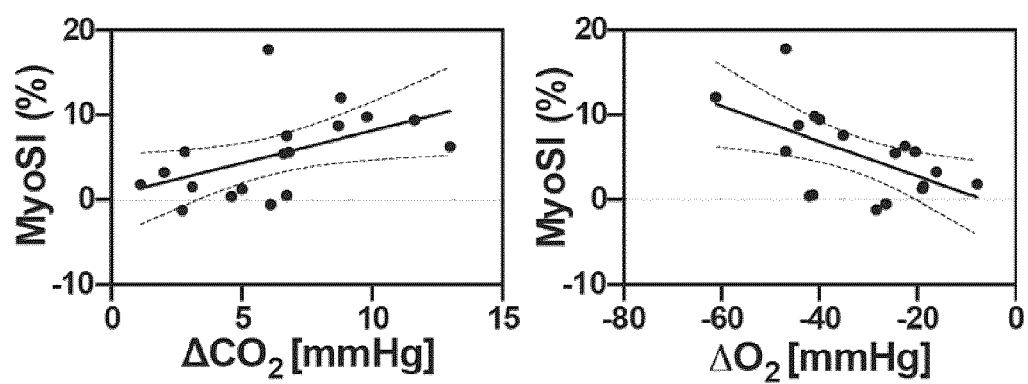
FIG. 7 shows a correlation of changes of myocardial SI with changes in capillary $pCO_2$ and a correlation between myocardial SI and changes in $paO_2$ levels in swine.

FIG. 7 shows a correlation of changes of myocardial SI and changes in capillary $pCO_2$ and correlation of myocardial SI and changes in the $paO_2$ levels in swine. For the normoxemic levels, correlations were present between myocardial SI and both $paCO_2$ (r=0.50, P=0.03) and $paO_2$ (r=−0.57, P=0.01). Multiple regression showed that both of these parameters could be combined to explain the changes in SI ($R^2$=0.42, $F_{2,15}$=5.43, P=0.02).

Figure 8:
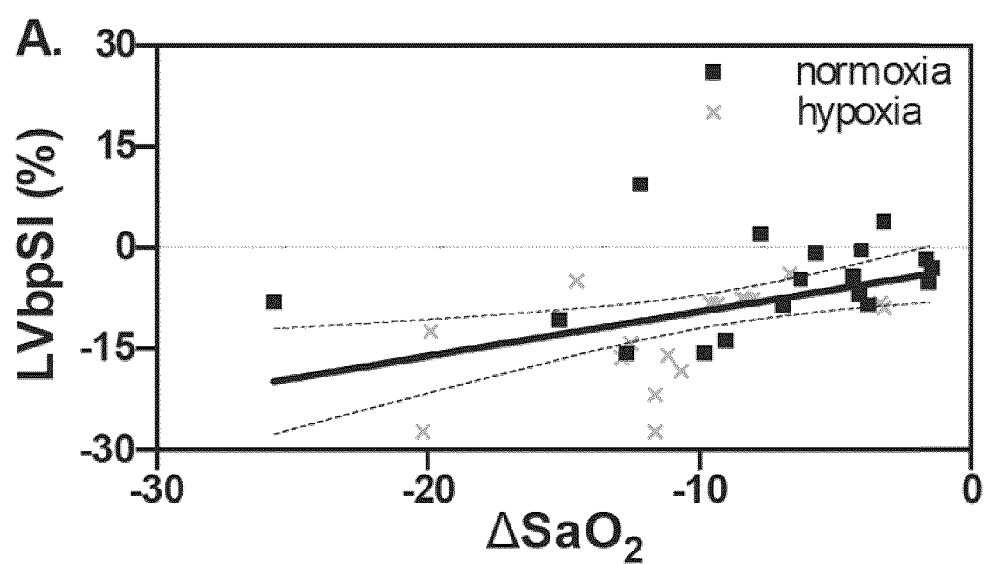
FIG. 8 shows a correlation of changes in left ventricular blood pool OS-SI with changes in $SaO_2$. The changes in $paO_2$ with the corresponding change in $SaO_2$ for the $pO_2$=100/$pCO_2$=50 mmHg versus the 80/50 mmHg level in swine.

FIG. 8 shows a correlation between changes in left ventricular blood pool OS-SI and changes in $SaO_2$. Blood pool OS-SI was found to be moderately correlated to the change in $SaO_2$ (r=0.46, P<0.01). Analysis of the myocardial SI was divided into hypoxemic and normoxemic levels. In the hypoxemic levels no relationship was observed between myocardial SI and any blood gases. The changes in $paO_2$ with the corresponding change in $SaO_2$ for the $pO_2$=100/ $pCO_2$=50 mmHg versus 80/50 mmHg level in swine.

Relationship of Signal Intensity to Cardiovascular Parameters

There was no correlation between myocardial BOLD-SI changes and heart rate or mean arterial blood pressure. However there was a moderate negative correlation between HR and left ventricular blood pool SI (r=0.47, P=0.049).

Example 3

Changes in Myocardial Oxygenation in Healthy Volunteers Performing Breathing Maneuvers Anaesthetics, which can affect coronary vascular tone, are a confounding factor in a model when trying to assess vascular function. It is possible that voluntary breathing maneuvers such as hyperventilation or a breath-hold can induce changes in myocardial oxygenation detectable by oxygen sensitive CMR.

Experimental Protocol

Eight healthy volunteers and six aquatic athletes were recruited to perform breathing maneuvers in a 1.5 T clinical MRI scanner (Siemens Avanto, Siemens, Erlangen Germany). Volunteers were required to be a minimum age of 18 years and provide informed consent. Aquatic athletes had to be able to comfortably hold their breath for at least 60 seconds. Exclusion criteria consisted of any conditions of previous or known cardiovascular disease, respiratory disease, vasoactive medication, pregnancy, consumption of coffee, tea or cigarettes 12 h prior to the scan, as well as general exclusion criteria for MRI exams. The healthy normal volunteers performed three breathing maneuvers; a free maximal breath-hold and two sets of hyperventilation of 1 and 2 minutes each. Aquatic athletes were asked to perform a timed 60 s breath-hold as well as a free maximal breath-hold. Using a 32-channel cardiac phased array coil, BOLD-sensitive steady-state-free-precession (SSFP) gradient echo cine images were continuously acquired during the breath-holds in mid left-ventricular short axis views (slice thickness 10 mm, TE 2.78 ms, TR 5.56 ms, FA 90°, FOV 280×157.5, matrix 128×72), (Vohringer et al. 2010; Guensch et al. 2012; Dharmakumar et al. 2006). For the acquisition of hyperventilation images, two baseline cines and two post-hyperventilation cines were acquired during a short breath-hold. Each cine loop was composed of 20 phases covering the entire cardiac cycle, obtained by retrospective ECG gating. Prior to and immediately after breathing maneuver, capillary $pO_2$ and $pCO_2$ were acquired. With respect to "immediately after" it is meant that the signal intensity is measured as soon as possible after the breathing maneuver is complete. It has been shown that the myocardial response to breathing maneuvers is diminished within three natural breaths after completion of the breathing maneuver. The hands were warmed to arterialize the blood.

Image Analysis

The images were analyzed with certified software for CMR images (cmr[42], Circle Cardiovascular Imaging Inc., Calgary, AB, Canada). Image quality was graded prior to SI measurement using visual assessment based on a 1-4 scale: 1=good image quality, 2=mildly impaired image quality resulting in <10% of the total myocardial area excluded, 3=limited image quality resulting in >10% of the myocardium or >1 phases from the cine to be excluded, 4=image with insufficient quality for analysis. The mean myocardial SI in the images was automatically calculated after manual tracing of endocardial and epicardial contours of all images. Additionally, left ventricular blood pool contours were traced to assess changes of SI caused by changes in arterial haemoglobin saturation (Guensch et al. 2012).

For the breath-hold experiments the first two cine series of the breath-hold were averaged for all cardiac phases and compared to the final two cines. If breath-holds were shorter resulting in four or less cine series, only the first cine was compared to the final one. For the hyperventilation experiments the two baseline scans were averaged accordingly and compared to two post-hyperventilation images. The area under the curve (AUC) was calculated from the signal intensity of all 20 phases and expressed as percent change SI from baseline to provide a single SI value incorporating representative data of the entire cardiac cycle.

All images were analyzed by two readers and the average change in myocardial SI from both readers was reported.

Statistical Analysis

To determine the SI changes resulting from the breathing maneuvers the AUC from the beginning of the breath-hold/before hyperventilation were compared to those at the end of the breath-hold or after hyperventilation, respectively, using a paired t-test and expressed as % change-SI. A one-way ANOVA and a Tukey-Kramer post-hoc test were used to compare the % change-SI between the different breathing maneuvers. Inter-observer variability of the MR analysis was assessed with an intraclass correlation. The changes in blood gases from baseline and after a breathing maneuver were analyzed using a paired t-test and correlation was calculated between the changes of BOLD-SI, blood gases and heart rate. A D'Agostino's-Pearson normality test was performed to assess normal distribution within the data points. Multiple regression analysis was performed with these variables using blood gases and heart rate as the independent variables and BOLD-SI as the response variable to determine which factor was primarily responsible for the variation in BOLD-SI. Additionally, analyses were also performed with normalization for heart rate (SI/HR). $P<0.05$ was regarded statistically significant. Statistical analysis was completed with SPSS version 19 (SPSS, Chicago, Ill.) and Graph Pad Prism (GraphPad Software, San Diego, Calif.).

Results

There were five breathing maneuver groups available for analysis: 1-minute hyperventilation (HV60 s, n=7), 2-minute hyperventilation (HV120 s, n=5), short free breath-hold (BH35 s, n=6), timed 60-second breath-hold (BH58 s, n=6) and long free breath-hold (BH117 s, n=5). In the HV60 s experiment, one volunteer had to be excluded due to insufficient image quality. In the HV120 s group, two studies had to be excluded due to poor image quality whereas one volunteer had to abort the experiment due to hyperventilation side effects. One volunteer was excluded from the timed 60 s breath-hold due to bad image quality. Subjects whose breathing maneuvers did not meet pre-defined criteria, were reallocated to the appropriate breathing maneuver group prior to image analysis.

Blood Gas Analysis

Capillary $pO_2$ dropped significantly by 16.3 mmHg after the longest breath-hold, BH117 s (P=0.04). There was no change in $pO_2$ observed in the other experiments. In both hyperventilation experiments there was a significant drop in capillary $pCO_2$ (Table 2).

TABLE 2

Changes of cardiovascular parameters at different blood gas baseline levels during a 60 s breath-hold in swine.

|  | n | $pO_2$ Baseline | $pO_2$ Post | p | $pCO_2$ Baseline | $pCO_2$ Post | p |
|---|---|---|---|---|---|---|---|
| Hyperventilation (120 s) | 5 | 56.8 ± 1.8 | 56.3 ± 3.7 | 0.738 | 29.0 ± 0.7 | 20.3 ± 0.4 | <0.001* |
| Hyperventilation (60 s) | 7 | 63.1 ± 4.2 | 61.7 ± 3.4 | 0.696 | 27.9 ± 1.5 | 22.0 ± 1.2 | 0.002* |
| Breath-hold (35 s) | 6 | 54.7 ± 2.7 | 62.0 ± 2.6 | 0.101 | 29.1 ± 1.3 | 29.3 ± 0.8 | 0.880 |
| Breath-hold (60 s) | 6 | 56.3 ± 4.0 | 62.1 ± 3.9 | 0.385 | 27.1 ± 2.4 | 27.9 ± 1.3 | 0.695 |
| Breath-hold (117 s) | 5 | 60.9 ± 2.4 | 44.6 ± 3.7 | 0.040* | 25.3 ± 2.8 | 27.7 ± 2.0 | 0.119 |

*Statistically significant

CMR Results

Figure 9:
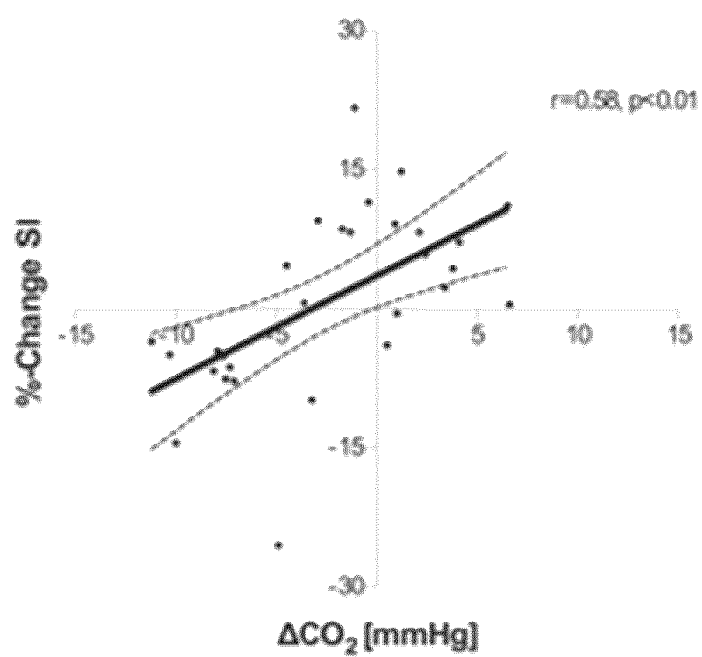
FIG. 9 shows changes in OS-SI in volunteers in response to breathing maneuvers.

FIG. 9 shows the changes in OS-SI in volunteers with different breathing maneuvers: 1 min hyperventilation, 2 min hyperventilation, free short breath-holds (normal volunteers), 1 min timed breath-hold as well as a long free breath-hold (aquatic athletes). In the 2 min (HV120 s) group, myocardial SI decreased by −7.5±1.8% (P=0.02). In contrast, myocardial SI increased by 8.2±2.8% (P=0.04) after the longest breath-hold (BH117 s). Although not significant, the HV60 s group shows a trend for a SI decrease, while an increase was observed in the BH35 s and BH58 s cohorts. A change in arterial blood SI in the left ventricle was only observed in the BH117 s group (−6.8%, P=0.02). ANOVA analysis showed a difference between at least two breathing maneuver groups when comparing the %-change in SI ($F_{4,24}$=4.7, P<0.01).

Statistical Results

Figure 10:
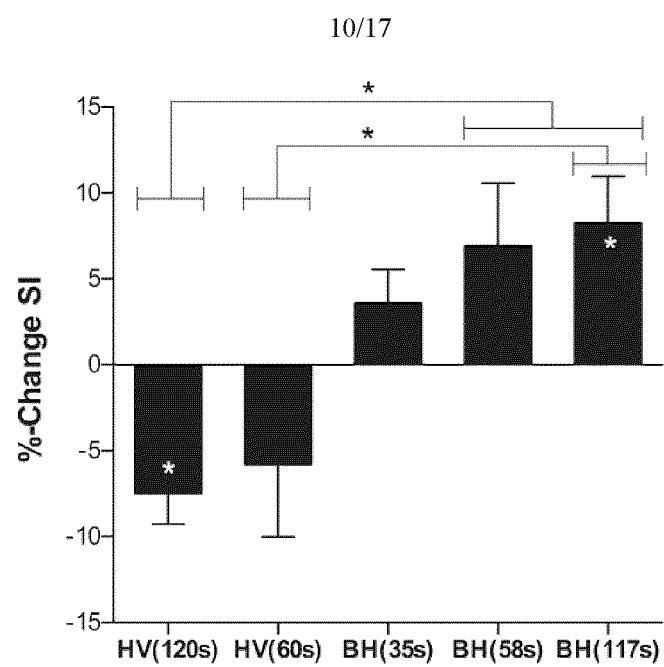
FIG. 10 shows a difference in $paCO_2$ (mmHg) plotted against the % change in myocardial SI in volunteers during breathing maneuvers.

FIG. 10 shows the statistical analysis of the difference in $paCO_2$ (mmHg) plotted against the % change in myocardial SI in volunteers during breathing maneuvers. The D'Agostino's-Pearson normality test showed a normal distribution within the data points. Both the $CO_2$ values and the myocardial SI changes passed the normality test. When variables were assessed individually, a correlation was found between myocardial SI and pCO2. A negative correlation was found between heart rate and both $CO_2$ (r=−0.62, P<0.01) and myocardial BOLD-SI (r=−0.43, P=0.02), but regression analysis showed the variance inflation factor (VIF) between $pCO_2$ and HR was <10 so the variables were assessed together in one model with multiple regression. While $pCO_2$, $pO_2$ and heart rate can explain changes seen in myocardial SI ($r^2$=0.35, $F_{3,25}$=4.4, P=0.01), $CO_2$ was the only variable which was independently correlated with myocardial SI changes. Moreover, there was no direct relationship found between the absolute myocardial SI and HR. When a correction for HR was performed, the relative SI change was more pronounced for both, breath-hold and hyperventilation experiments. With these values corrected for heart rate, the increases in SI after each breath-hold was significantly different from the changes caused by hyperventilation ($F_{4,24}=8.8$, $P<0.05$). ANOVA showed a stronger correlation with $pCO_2$ changes, when SI was corrected for heart rate ($r=0.68$, $P<0.01$).

Image Quality

Out of 33 scans, 13 (39%) were graded as good, with the highest score of 1. Images with minor artifacts were graded medium image quality (n=13, 39%) and three images were graded as poor (n=3, 9%), resulting in 29 of the 33 scans being analyzable (88%). Four studies (12%) were non-analyzable due to breathing artifacts and thus excluded from the analysis. Intraclass correlation between the two observers was excellent (ICC=0.90, [0.80; 0.95]).

Example 4

Assessing Microvascular Function with Breathing Maneuvers in Healthy Volunteers: An Oxygenation-Sensitive 3 T-CMR Approach Summary This study compares the effects of breathing maneuvers (breath-holds, hyperventilation), a combination of the two maneuvers (referred to as hyperventilation-breath-holds) in healthy volunteers at 3 Tesla and compares this to the current gold standard adenosine to induce coronary hyperaemia.

Methods

Experimental Protocol

Fourteen healthy subjects were recruited to perform breathing-maneuvers and undergo intravenous adenosine infusion in a 3.0 T clinical MRI scanner (Siemens MAGNETOM Skyra, Siemens, Erlangen Germany) at the Montreal Heart Institute. Volunteers were required to have a minimum age of 18 years and be able to give informed consent. Exclusion criteria were any conditions of known cardiovascular or respiratory disease, medication with vasoactive effects, pregnancy, consumption of coffee, tea or cigarettes 12 h prior to the scan, as well as general exclusion criteria for MRI exams such as implanted ferromagnetic objects and claustrophobia.

Figure 11:
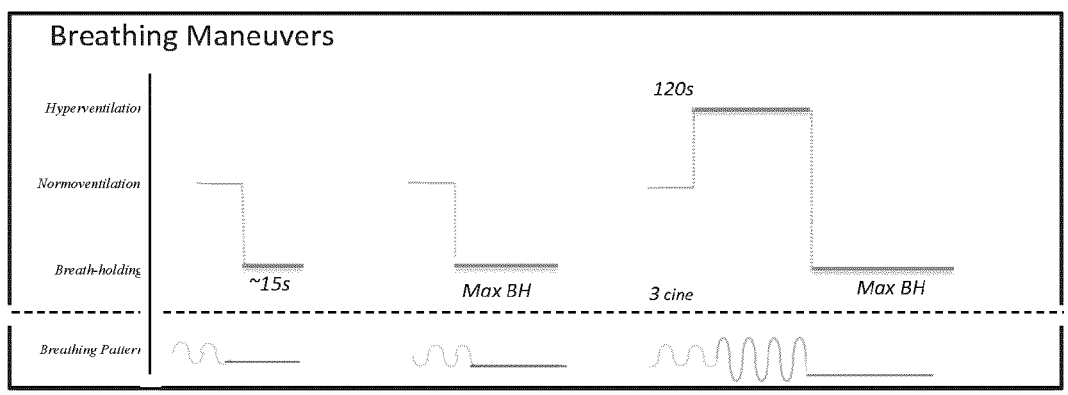
FIG. 11 is an illustration of breathing maneuvers that may used in the method disclosed herein.

FIG. 11 is an illustration of exemplary breathing maneuvers that may be used with the method disclosed herein. The left panel shows a 15-20 s breath-hold; the middle panel shows a maximal breath-hold from baseline breathing; and the right panel shows a 120 s period of hyperventilation followed by a maximal breath-hold.

MRI Protocol

The OS images are an ECG-triggered steady state free precession (SSFP) and acquire 15-25 images across the cardiac cycle, thus allowing a specific phase to be chosen (flip angle: 35, temporal resolution: 42.6 ms, echo time: 17.78 ms, echo spacing: 3.4 ms). These images were obtained for 1 SAX slice in the mid-left ventricle. Three breathing maneuvers were performed. A baseline OS-SSFP image with one measurement was obtained at baseline. After which the volunteer hyperventilated for 60 s and then performed a maximal long breath-hold (HVBH) for as long as they could without diaphragm motion. With time to normalize in between maneuvers volunteers performed a timed 20 s breath-hold (BH20 s) and a maximal long breath-hold from normal respiration (LBH). OS-SSFP with multiple measurements imaged throughout the entire breath-holds.

For the adenosine infusion OS-SSFP images with 1 measurement were acquired at baseline and between 2:30-3:30 min after the start of continuous infusion of a standard dose of adenosine (140 µg/kg/min).

Throughout each procedure heart rate and $SpO_2$ monitored with a pulse oximeter on the finger were recorded.

Post-Exam Questionnaire

After the exam, volunteers completed a questionnaire in which they were asked to rank the difficulty of each maneuver. Each question also asked if side effects occurred and if they disappeared once the maneuver was done, and to describe any side effects.

When asked to rank the maneuvers, adenosine was ranked last, LBH and HVBH were tied, although the differences were not significant, and the BH20 s was ranked as significantly the easiest maneuver (*$p<0.01$). Of these 12 volunteers, 7 experienced side effects in response to adenosine including tightness in the chest, difficulty breathing and increased heart rate. All side effects disappeared once the drug infusion was stopped. None of the side effects seen with adenosine treatment were experienced in response to breathing maneuvers.

Image-Analysis

The images were analyzed with certified software for CMR image analysis (cvi$^{42}$®, Circle Cardiovascular Imaging Inc., Calgary, AB, Canada). The mean myocardial SI in the BOLD-sensitive images was automatically calculated after manual tracing of endocardial and epicardial contours in all images of each cine series. The myocardium was further split up into the AHA based segmentation. Automatic software segmentation was performed after user-define posterior and exterior insertion points. Additionally, left ventricular blood pool contours were traced in order to assess changes in arterial haemoglobin saturation. As OS-SSFP imaging obtains 15-25 images for each cardiac cycle, only OS-SI from systole was used for analysis. End-systole was chosen to analyze as there is more myocardium in the imaging plane providing more voxels and a greater change in signal. During the extended breath-holds multiple measurements are acquired in one series. Thus data is assessed as the change in SI over time and both the final %-change in SI is presented as well as the value and time when the myocardial SI peaked at its highest value.

Reporting of Image Quality

Images were graded a score of 1 to 4 dependent on the readers visual interpretation: 1=good image quality, 2=mildly impaired image quality resulting in 5-15% of the myocardium excluded, 3=limited image quality resulting in >15% area exclusion or >1 excluded segment, 4=non-analyzable image. Individual segments were excluded if >33% of the segment area was excluded.

Statistical Analysis:

Data is expressed as mean±SEM. Paired t-tests were used to compare signal intensity from the start and end of a maneuver. ANOVA was used to assess the difference between groups. For the long breath-holds with signal plotted over time, a non-linear regression was performed along with providing the max peak, and slope of the increase. Both of these values may be used to distinguish healthy versus ischemic tissue. The ranking of the maneuvers of the questionnaires was analyzed with a Friedman's non-parametric test. Statistical analysis was completed with SPSS version 21 (SPSS, Chicago, Ill.) and Graph Pad Prism (GraphPad Software, San Diego, Calif.).

Results

Twelve volunteers successfully completed the exam as one was excluded because of pre-existing sleep apnea and the other withdrew at the beginning of the exam because of claustrophobia (n=12).

CMR Results

Figure 12:
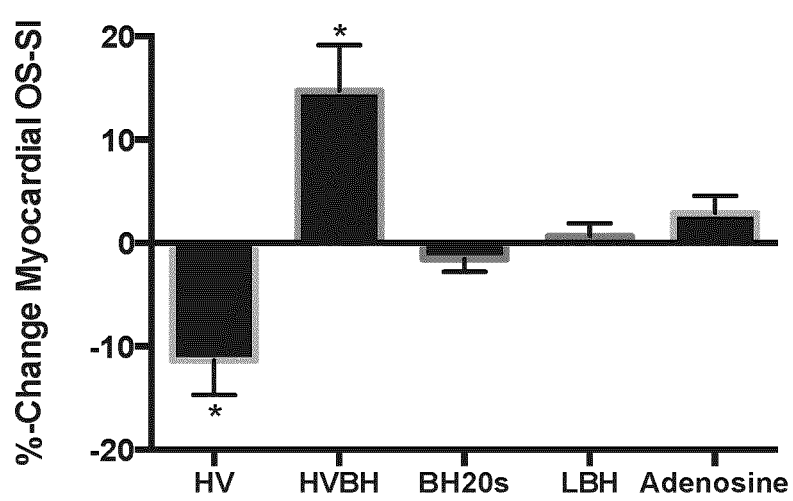
FIG. 12 shows the %-change of myocardial SI in response to breathing maneuvers compared to % change of myocardial SI in response to adenosine (n=12, *p<0.05)

FIG. 12 shows a comparison between the change in myocardial SI induced by hyperventilation alone (HV), hyperventilation followed by breath-hold (HVBH), a 20 s breath-hold (BH20 s), a long breath-hold (LBH) and that induced by adenosine. The %-change between the beginning and end of each maneuver is shown for the HVBH, BH20 s, LBH, and adenosine (n=12, *p<0.05). When assessing global myocardial SI, the gold standard method of using adenosine to induce vasodilation caused an increase of 2.9±1.7%. Significant changes were observed in response to some of the breathing maneuvers. For example, the SI change induced by hyperventilation was a decrease by 11.4±3.3% (*p=0.01), whereas the SI change from the beginning to end of the subsequent breath-hold was an increase of 14.7±4.4% (*p<0.01). Additionally this increase from the breath-hold after hyperventilation (HVBH) was significantly greater than observed with adenosine (*p=0.02) and the long breath-hold (LBH). Both the HVBH and LBH were maximal breath-holds, but after HVBH the mean time of the breath-hold was 62.4±5.7 s, and 49.7±19.3 s after the breath-hold starting from a normal breathing rate. The long breath-hold or the 20 s breath-hold from normal respiration did not show a difference when comparing the start and end point.

Figure 13:
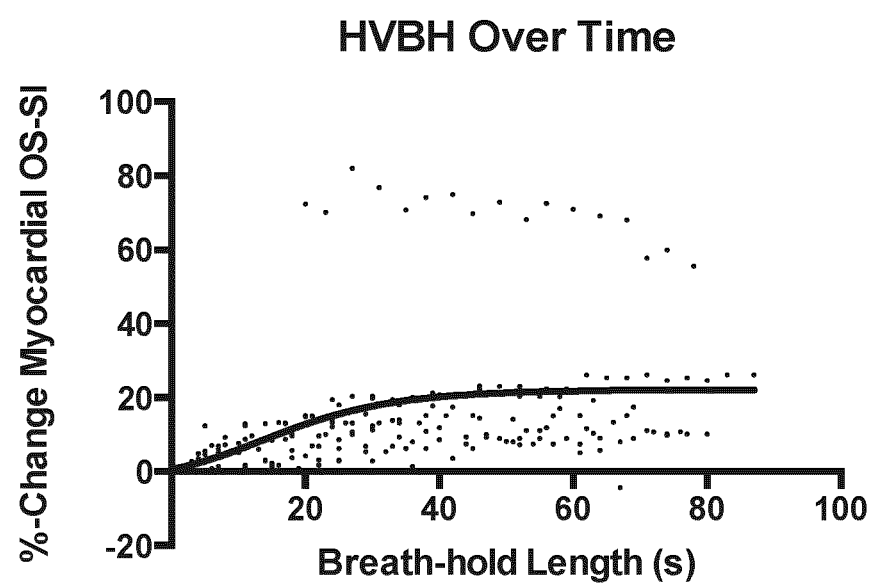
FIG. 13 shows the change in SI over time in response to hyperventilation and breath-holds HVBH compared to the SI in an image at the start of the breathing maneuvers (n=12) with a non-linear regression line.

FIG. 13 shows the change in SI over time of the HVBH compared to the image at the start of the maneuver (n=12) with a non-linear regression line.

Image Quality

No full images were excluded due to image quality and the scores ranged from 1-3 for each image: HV baseline image (1: n=3, 2: n=8, 3: n=1), HVBH (1: n=1, 2: n=8, 3: n=3), BH20 s (1: n=6, 2: n=6, 3: n=0), LBH (1: n=2, 2: n=8, 3: n=2), and the pre-adenosine (1: n=2, 2: n=8, 3: n=2) and post-adenosine (1: n=2, 2: n=9, 3: n=1).

Fourteen volunteers participated in a 3 T MRI study, twelve of which resulted in analyzable data. Hyperventilation decreased SI by 11.4±3.3% whereas the following breath hold increased the SI by 14.7±4.4%. This change from the breath-hold was significantly greater than the change observed with adenosine, which is the current clinical gold standard for inducing myocardial hyperaemia. Furthermore, the volunteers on the questionnaire ranked breathing maneuvers easier to perform than adenosine. When the SI of the breath-hold was assessed over time, the peak myocardial SI occurred prior to the end of the breath-hold, after which a plateau or even a decrease was observed.

Example 5

Cardiovascular Response of Myocardial Oxygenation to Breathing Maneuvers in Swine: An Oxygenation-Sensitive 3 T-CMR Approach Most oxygenation-sensitive studies are based on the assumptions of the roles of coronary blood flow and hemoglobin saturation on CMR signal. This study obtains invasive measurements of the left anterior descending (LAD) coronary artery flow and both arterial and coronary sinus blood samples to assess blood gas levels. These parameters are correlated to OS-SI and used to compare the response in signal of breathing maneuvers to manually altered blood gas levels and to adenosine.

Methods

Animal Procedure Protocol

Ten anaesthetized swine (30-35 kg) underwent CMR imaging in a 3.0 T clinical scanner (Siemens MAGNETOM Skyra, Siemens, Erlangen Germany). Animals were pre-medicated with Telazol (6 mg/kg) and atropine (0.8 mg), induced with 2-3 mg/kg propofol to reach an appropriate anaesthesia depth, intubated and mechanically ventilated. Anesthesia was maintained with continuous administration of 12-20 mg/kg/h propofol and remifentanil for analgesia 0.5-2.0 µg/kg/h. A sternotomy was performed to provide direct access to the heart so that a perivascular flow probe (2.5 mm, Transonic Systems, Inc., Ithica, N.Y.) could be placed directly on the proximal LAD. Venous catheters were placed for drug administration as well as a sheath was placed both in the femoral artery and directly in the coronary sinus to obtain blood samples. Quantitative coronary angiography (QCA) was obtained after the procedures to verify coronary artery stenosis was not created with the flow probe placement.

Figure 14:
FIG. 14 is a coronary angiography image displaying the placement of a perivascular flow probe on the left LAD of a healthy animal.

FIG. 14 is a coronary angiography image displaying the placement of a perivascular flow probe on the LAD of a healthy animal.

CMR Imaging Protocol

The majority of OS images are an ECG-triggered steady state free precession (SSFP) and acquire 15-25 images across the cardiac cycle, thus allowing a specific phase to be chosen (flip angle: 35, temporal resolution: 42.6 ms, echo time: 17.78 ms, echo spacing: 3.4 ms). These images were obtained for three short axis (SAX) slices, from the mid ventricle to the apex. An OS colour map was also used imaging only in the systolic phase off 1 mid-SAX slice (ECG triggered, flip angle: 35, temporal resolution: 238.1 ms, echo time: 1.06 ms, echo spacing: 2.5 ms). This map is a OS-sensitive T2*/T2 map formulated from three data points of a single-shot T2-prepared TrueFisp sequence. A standard retrograde cine was used for the function, which was scanned using 10-12 slices in a SAX stack (flip angle: 65, temporal resolution: 39.24 ms, echo time: 1.43 ms, echo spacing: 3.3 ms).

Experimental Protocol

Nine different blood gas levels were achieved and stabilized by manipulating ventilation rate, tidal volume and the inspiratory gas concentration achieved by a mix of a pure oxygen, medical air and nitrogen. These levels were composed of a $paCO_2$ of hypocapnia (30 mmHg), normocapnia (40 mmHg) or hypercapnia (50 mmHg) with a $paO_2$ level of hypoxia (70 mmHg), normoxia (100 mmHg) or hyperoxia (>250 mmHg). A targeted level was verified with on-site blood gas analysis of the arterial blood. At each level left ventricular function, oxygenation-sensitive SSFP and oxygenation-sensitive maps were acquired. For each measurement the following parameters were recorded when the OS images were obtained: the blood flow (ml/min) of the LAD was measured in addition to invasive blood pressure, end-tidal $CO_2$ gas pressure, heart rate, and $SpO_2$ measurements. Blood samples of both the arterial and coronary sinus blood gas were analyzed for partial pressures of $O_2$ and $CO_2$, as well as pH, hemoglobin saturation ($SO_2$), hemoglobin concentration (Hb) and hematocrit (Hct).

After the completion of the nine-targeted levels, a breathing maneuver protocol was performed. As the breathing maneuver involved transient and not stable blood gas levels, only the OS-SSFP images were obtained. The imaging occurred continuously throughout the breath-hold with an acquisition every 3.5 s. Immediately after new baseline measurements, the animal underwent a 90 s breath-hold at end expiration followed immediately by post-breath-hold measurements. The second breathing maneuver involved 60 s of hyperventilation from baseline values followed by a 90 s breath-hold.

For a vasodilatory control, adenosine was infused intravenously for 4 minutes at a dose of 140 µg/kg/min. Measurements and OS-SSFP images and OS-maps were obtained at baseline and at 3 minutes after the start of infusion. After allowing at least 10 minutes for adenosine to wash-out, endothelin-1 (ET-1) was infused intravenously for 10 minutes at 50 ng/kg/min. Measurements and OS-SSFP images and OS-maps were obtained at baseline, 6 and 9 minutes after the start of infusion. The animal was sacrificed with a bolus of both 200 mg propofol and 40 mmol KCl.

Image Analysis

The images were analyzed with certified software for CMR image analysis (cvi$^{42}$®, Circle Cardiovascular Imaging Inc., Calgary, AB, Canada). The mean myocardial SI in the BOLD-sensitive images was automatically calculated after manual tracing of endocardial and epicardial contours in all images of each cine series. The myocardium was further automatically split up into the AHA based segmentation by manually defining the anterior and posterior right ventricular insertion point. Additionally, left ventricular blood pool contours were traced in order to assess changes in arterial haemoglobin saturation. As OS-SSFP imaging obtains 15-25 images for each heart beat (cardiac cycle), only OS-SI from systole was used for analysis. During the extended breath-holds multiple measurements are acquired in one series. Thus data is assessed as the change in SI over time and both the final %-change in SI is presented as well as the value and time when the myocardial SI peaked at its highest value.

Statistical Analysis:

Data is expressed as mean±SEM. Paired t-tests were used to compare signal intensity from the start and end of a maneuver. ANOVAs were used to assess the difference between groups. For the long breath-holds with signal plotted over time, a non-linear regression was performed along with providing the max peak, and slope of the increase. Data is considered significant if $p<0.05$. Statistical analysis was completed with SPSS version 21 (SPSS, Chicago, Ill.) and Graph Pad Prism (GraphPad Software, San Diego, Calif.).

Figure 15:
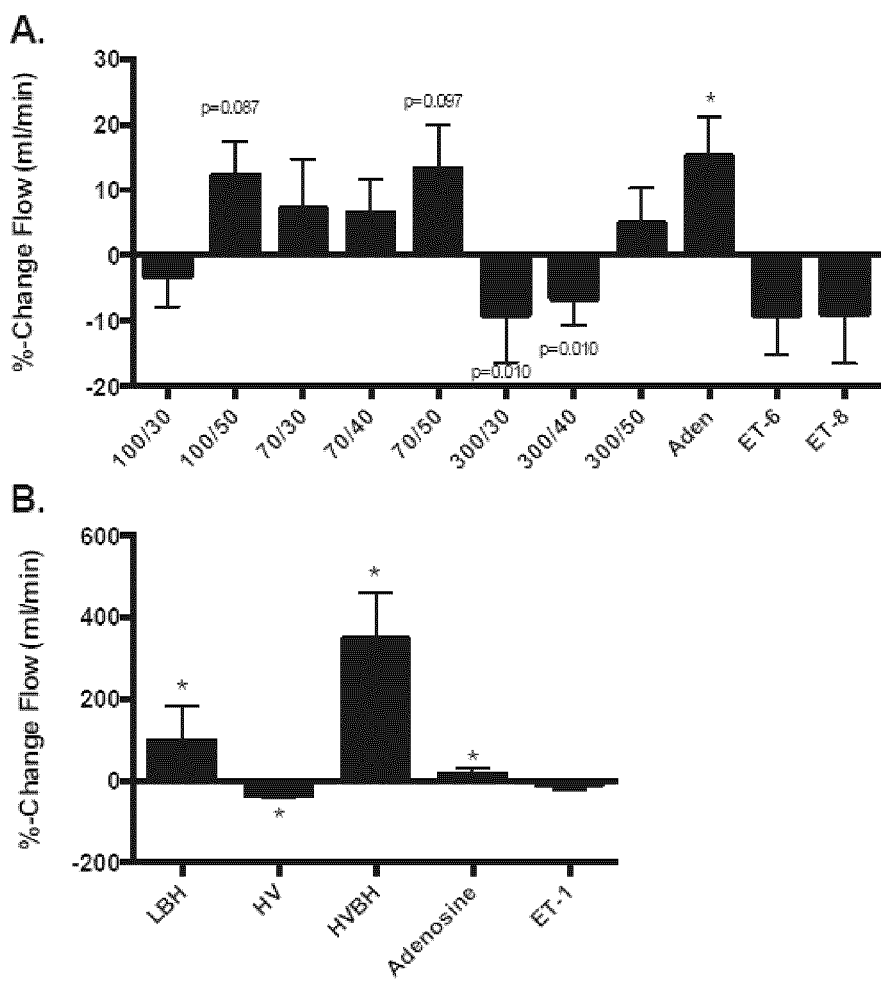
FIG. 15 shows the %-change in coronary flow from baseline levels as measured by a perivascular flow probe placed on the LAD (*p<0.05, n=8)

FIG. 15 shows the %-changes in coronary flow from baseline levels as measured by a perivascular flow probe placed on the LAD (*$p<0.05$, n=8). A) The %-change induced by altered blood gas levels compared to adenosine (aden-)- and ET-6 and ET-8-induced changes, B) The change of coronary blood flow in response to breathing maneuvers (90 s breath-hold (LBH); 60 s hyperventilation (HV); and a 60 s hyperventilation followed by a 90 s breath-hold (HVBH) in comparison to % change in blood flow in response to adenosine and ET-1. The breathing maneuvers caused significant changes in flow (*$p<0.02$). In response to hyperventilation, flow decreased by 34.0±8.1%, while the flow increased 96.7±31.0% in response to LBH and increased 346.1±115.6% in response to HVBH. These increases were more pronounced than the response induced by the drugs. For instance, adenosine increased flow by 15.1±6.2% (*$p=0.03$) and ET-1 decreased flow non-significantly by 9.1±6.1%. In addition, no significant changes in blood flow were observed in response to alterations in blood gas levels. Thus, breathing maneuvers are more effective at increasing blood flow when compared to vasodilators or manipulating $CO_2$ levels in the blood.

Figure 16:
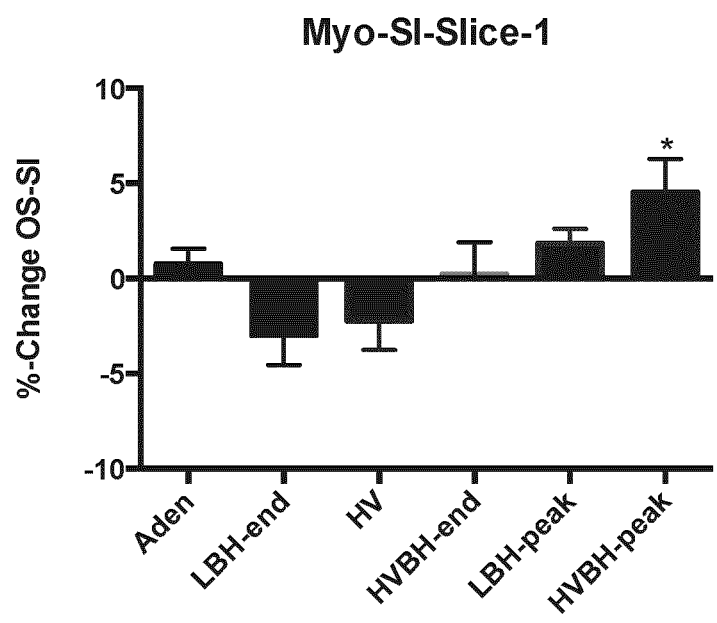
FIG. 16. shows the %-change of myocardial SI in response to breathing maneuvers obtained from a mid-apical slice of an image of a heart.

FIG. 16 shows the peak %-change in SI of OS-SSFP images from the mid and mid-apical myocardium in response to breathing maneuvers (n=8, *$p<0.05$). The peak change in signal intensity was the value that was the highest during the maneuver.

Figure 17:
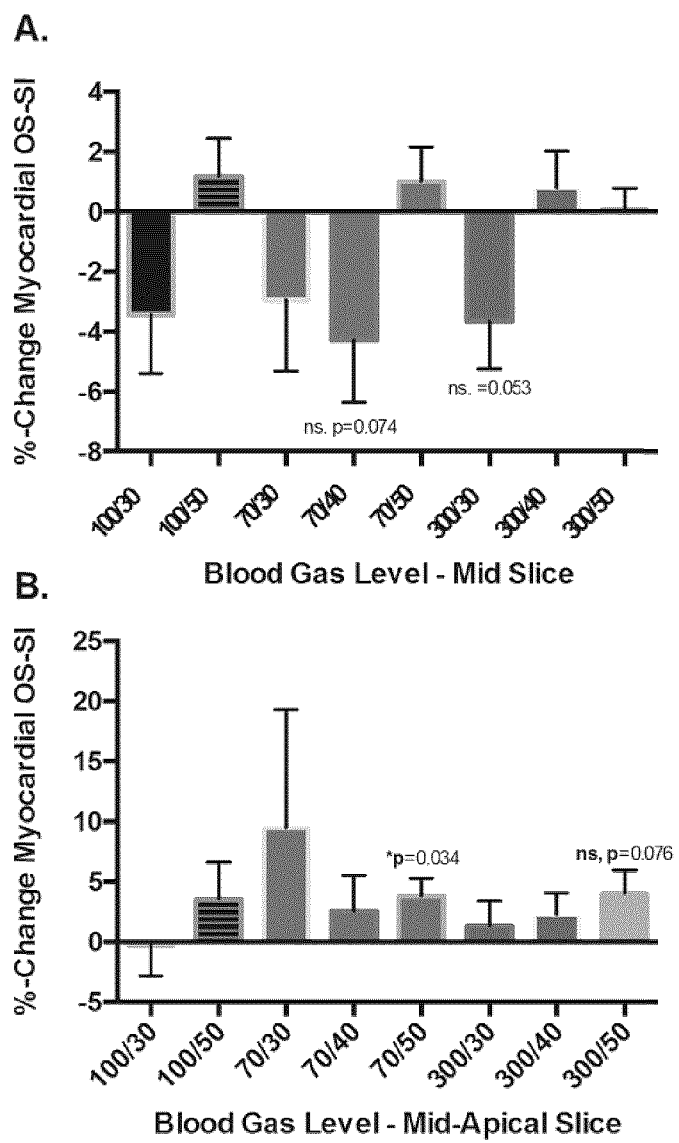
FIG. 17 shows the %-change of myocardial SI in a mid slice and a mid-apical slice in comparison to the baseline of $paO_2$=100 mmHg and $paCO_2$=40 mmHg.

FIG. 17 shows the %-change of myocardial SI from mid slice and mid-apical slices of the myocardium in response to changes in blood-gas levels in comparison to the baseline of $paO_2=100$ mmHg and $paCO_2=40$ mmHg (100/30, 100/50=normoxic; 70/30, 70/40, 70/50=hypoxic; 300/30, 300/40, 300/50=hyperoxic) Table 3 shows the mean (SEM) %-change in global myocardial OS-SI of each blood gas level in comparison to baseline, 100/40 as shown in FIG. 17 (n=8, *$p<0.05$). Slice 1 is a mid-SAX slice and slice 2 is a mid-apical SAX slice.

TABLE 3

| Blood Gas | Myocardial OS-SI (%-change) | |
| --- | --- | --- |
| Levels | Slice 1 | Slice 2 |
| 100/30 | −3.4 (2.0) | −0.3 (2.5) |
| 100/50 | 1.2 (1.3) | 3.5 (3.1) |
| 70/30 | −2.9 (2.4) | 9.5 (9.8) |
| 70/40 | −4.3 (2.1) | 2.5 (3.0) |
| 70/50 | 1.0 (1.2) | 3.8 (1.5)* |
| 300/30 | −3.7 (1.6) | 1.3 (2.1) |
| 300/40 | 0.8 (−2.1) | 2.3 (1.8) |
| 300/50 | 0.1 (0.7) | 4.0 (1.9) |

Similarly to the blood flow experiments, it was shown that the % change of myocardial oxygenation was increased in response to breathing maneuvers when compared to the % change in response to alterations of blood levels of $CO_2$ and $O_2$.

The results of Blood Gas analysis studies are shown in Table 4.

TABLE 4

| | O2er | MvO2 | Heart Rate |
| --- | --- | --- | --- |
| Blood Gas Levels | | | |
| 100/30 | 0.99 (0.88) | 16.7 (26.1) | −5.0 (12.8) |
| 100/50 | 0.42 (0/96) | 41.2 (13.2) | 2.6 (2.7) |
| 70/30 | 1.74 (0.83) | 57.9 (23.3) * | 2.1 (14.7) |
| 70/40 | 1.53 (0.46) * | 51.8 (23.3) | 12.8 (5.3) |
| 70/50 | 0.80 (0.38) | 43.9 (17.9) | 9.3 (3.0)* |
| 300/30 | 0.64 (1.24) | −15.5 (31.2) | 4.3 (6.4) |
| 300/40 | −0.12 (1.0) | −12.8 (32.7) | −3.9 (5.6) |
| 300/50 | 3.21 (3.5) | 65.2 (73.6) | −3.5 (4.8) |
| Breathing Maneuvers | | | |
| HV | −1.21 (1.04) | −109.6 (44.6) | −8.7 (11.6) |
| HVBH | 0.86 (1.36) | 322.3 (80.9) * | 13.7 (9.4) |
| LBH | −2.11 (0.91) | 59.3 (72.8) | 18.3 (13.2) |
| Control Drug Infusion | | | |
| Adenosine | −0.16 (0.39) | 20.6 (15.8) | −3.4 (1.2)* |
| ET-1 | −0.11 (0.27) | −30.9 (14.3) | −12.2 (3.9)* |

Mean (SEM) delta changes of oxygen extraction ($O_2$er) and myocardial oxygen consumption ($MvO_2$) were calculated using the arterial and coronary sinus blood gas measurements and the LAD flow measurements, as well as the heart rate (n=8, *$p<0.05$).

Arterial $pCO_2$ and $pO_2$ were manually set to a desired blood gas levels. $PaCO_2$ changed for the LBH 14.5%, HV −15.3%, HVBH 25.5%, while paO2 for these levels changed for the LBH −73% HV+73%, and −119% for the HVBH. These values did not change during the control drug infusions of adenosine and ET-1.

CMR Results

Animals underwent an involuntary breath-hold and were not able to restart breathing when desired. Thus blood gas analysis showed a large desaturation in arterial blood. For the breath-holds, both the %-change from the baseline to the end is plotted as well as from baseline to the peak myocardial SI within the breath-hold.

Table 5 shows the %-change in SI of the OS-SSFP images from the mid slice from the breathing maneuvers (n=8, *p<0.05).

TABLE 5

| Maneuver | Myocardium | Blood Pool | Corrected |
|---|---|---|---|
| Hyperventilation | −2.2 ± 1.5 (ns p < 0.10) | 1.5 ± 1.3 | −3.7 ± 1.6 (ns p < 0.10) |
| Hyperventilation Breath-hold | | | |
| End value | 0.22 ± 1.7 | −14.4 ± 2.4* | 14.6 ± 2.3* |
| Peak Value | 4.5 ± 1.8* | −9.4 ± 1.8* | 14.0 ± 2.1* |
| Long Breath-hold | | | |
| End value | −3.0 ± 1.6 | −19.6 ± 4.3* | 16.7 ± 4.3* |
| Peak Value | 1.8 ± 0.8* | −6.6 ± 2.1* | 8.5 ± 2.2* |

As both the volunteer data (example 4) and animal data (example 5) show, the breathing maneuvers show a more consistent and significantly greater OS-SI increase than adenosine. Adenosine is the current clinical gold-standard method of inducing myocardial hyperemia. By incorporating both hyperventilation and a breath-hold, subjects experience a greater range of $CO_2$ changes, which is reflected in the greater changes in OS-SI when combining the vasoconstrictive and vasodilative properties of both maneuvers. In a preferred embodiment, prior hyperventilation enables sufficiently long breath-holds that result in a significant change in OS-SI.

In addition, the data show that breath-holds lead to a consistent increase in myocardial blood flow, which leads to a decrease of the myocardial de-oxyhemoglobin fraction, which can be detected by OS-sensitive imaging in both an anaesthetized ventilated porcine model as well as in healthy volunteers performing breath-holds. In volunteers, controlled hyperventilation leads to a drop in myocardial OS-SI indicating an increased relative fraction of de-oxyHb due to hypocapnic vasoconstriction and/or increased myocardial workload. Further, the data indicates that breathing maneuvers are a much stronger stimulus than merely adjusting target blood gas levels. Without being bound by theory, it is possible that there may be an additive effect of desaturation as well as regulatory mechanisms of the autonomous nervous system that lead to the observed increased SI change.

The invention being thus described, it will be obvious that the same may be varied in many ways. Such variations are note to be regarded as a departure for the spirit and scope of the invention, and all such modifications would be obvious to one skilled in the art intended to be included within the scope of the following claims.

REFERENCES

Bauer, Wolfgang R., Walter Nadler, Michael Bock, Lothar R. Schad, Christian Wacker, Andreas Hartlep, and Georg Ertl. 1999. "Theory of Coherent and Incoherent Nuclear Spin Dephasing in the Heart." *Physical Review Letters* 83 (20) (November 15): 4215-4218. doi:10.1103/PhysRevLett.83.4215.

Dharmakumar, Rohan, Xiuling Qi, Juimiin Hong, and Graham A Wright. 2006. "Detecting Microcirculatory Changes in Blood Oxygen State with Steady-state Free Precession Imaging" *Magnetic Resonance in Medicine* 55 (6) (June 1): 1372-1380. doi:10.1002/mrm.20911.

Fieno, David S., Steven M. Shea, Yongzhong Li, Kathleen R. Harris, J. Paul Finn, and Debiao Li. 2004. "Myocardial Perfusion Imaging Based on the Blood Oxygen Level-Dependent Effect Using T2-Prepared Steady-State Free-Precession Magnetic Resonance Imaging." *Circulation* 110 (10) (September 7): 1284-1290. doi:10.1161/01.CIR.0000140673.13057.34.

Friedrich, Matthias G, and Theodoros D Karamitsos. 2013. "Oxygenation-sensitive Cardiovascular Magnetic Resonance." *Journal of Cardiovascular Magnetic Resonance* 15 (1) (May 24): 43. doi:10.1186/1532-429X-15-43.

Friedrich, Matthias G, Thoralf Niendorf, Jeanette Schulz-Menger, C Michael Gross, and Rainer Dietz. 2003. "Blood Oxygen Level-dependent Magnetic Resonance Imaging in Patients with Stress-induced Angina." *Circulation* 108 (18) (November 4): 2219-2223. doi:10.1161/01.CIR.0000095271.08248.EA.

Guensch, D P, K Fischer, J Flewitt, and M G Friedrich. 2012 "Impact of Intermittent Apnea on Myocardial Tissue Oxygenation—A Study Using Oxygenation-sensitive Cardiovascular Magnetic Resonance." *PLoS ONE* (in press). in Press.

Kelman, G R. 1966. "Digital computer subroutine for the conversion of oxygen tension into saturation." *Journal of applied physiology* 21 (4) (July): 1375-1376.

Severinghaus, J. W. 1979. "Simple, Accurate Equations for Human Blood 02 Dissociation Computations." *Journal of Applied Physiology* 46 (3) (March 1): 599-602.

Shea, Steven M, David S Fieno, Brian E Schirf, Xiaoming Bi, Jie Huang, Reed A Omary, and Debiao Li. 2005. "T2-Prepared Steady-State Free Precession Blood Oxygen Level-Dependent MR Imaging of Myocardial Perfusion in a Dog Stenosis Model1." *Radiology* 236 (2) (August 1): 503-509. doi:10.1148/radiol.2362040149.

Varjavand, N. 2000. *Oxyhemoglobin Dissociation Curve.* www.ventworld.com/resources/oxydisso/dissoc.html.

Vohringer, Matthias, Jacqueline Flewitt, Jordin Green, Rohan Dharmakumar, Jiun Wang, John Tyberg, and Matthias Friedrich. 2010. "Oxygenation-sensitive CMR for Assessing Vasodilator-induced Changes of Myocardial Oxygenation." *Journal of Cardiovascular Magnetic Resonance* 12 (1): 20. doi:10.1186/1532-429X-12-20.

Wacker, Christian M., Michael Bock, Andreas W. Hartlep, Gabriele Beck, Gerhard van Kaick, Georg Ertl, Wolfgang R. Bauer, and Lothar R. Schad. 1999. "Changes in Myocardial Oxygenation and Perfusion Under Pharmacological Stress with Dipyridamole: Assessment Using T*2 and T1 Measurements." *Magnetic Resonance in Medicine* 41 (4): 686-695. doi:10.1002/(SICI)1522-2594(199904)41: 4<686::AID-MRM6>3.0.CO; 2-9.

Mason, R. P., 2006. Non-invasive assessment of kidney oxygenation: a role for BOLD MRI. Kidney Int., 70(1): 10-11.

Morita N., Harada, M., Uno, M., Matsubara, S., Matsuda, t., Nagahiro, S., Nishitani, H. 2002. Ischemic findings of T2* weighted 3-telsa MRI in acute stroke patients. Cerebrovasc Dis. 26: 367-75.

Tamara, H., Hatazawa, J., Toyoshima, H., Shimosegawa E., Okudera T. 2002. Detection of deoxygenation-related signal change in acute ischemic stroke patients by T2*-weighted magnetic resonance imaging. Stroke, 33: 967-71.

Brown, J. M., Wilson, W. R. Exploiting Tumour Hypoxia in Cancer Treatment. 2004 Nat. Rev. Cancer. 4: 437-447.

Christen, T., Bolar, D. S., Zaharchuk, G. 2012. Imaging brain oxygenation with methods, validation and clinical applications. AJNR Am J. Neuroradiol: MRI using blood oxygenation approaches.

Utz, w., Jordan, J., Niendorf, T., Stoffels M., Luft, F. C., Dietz, R and Friderich, M. 2005. Blood oxygen level-dependent MRI of tissue oxygenation: relation to endothelium-dependent and endothelium-independent blood flow changes. Arterioscl Thromb. Vasc Biol. 25: 1408-1413.

What is claimed is:

1. A method of assessing heart function in a subject comprising:
   measuring a change in at least one of oxygenation and blood flow in the heart of the subject in response to at least one breathing maneuver;
   comparing the change in the at least one of measured oxygenation and blood flow to a control; and
   assessing heart function in accordance with the comparison result, wherein an abnormal response in at least one of oxygenation and blood flow in the heart compared to the control is indicative of reduced heart function.

2. The method of claim 1,
   wherein measuring the change comprises:
   imaging the heart, while oxygenation of the heart is altered in response to the at least one breathing maneuver, to produce an image,
   segmenting the image, and
   determining a signal intensity of a region of interest in a segment of the image;
   wherein comparing the change comprises comparing the signal intensity to a control; and
   wherein assessing heart function comprises assessing heart function in accordance with the comparison result, wherein an abnormal change in the signal intensity is indicative of reduced heart function.

3. The method of claim 1, wherein the breathing maneuver comprises a breath-hold.

4. The method of claim 3, wherein the breathing maneuver further comprises at least one period of hyperventilation.

5. The method of claim 3, wherein the breath-hold is voluntary.

6. The method of claim 3, wherein the breath-hold is induced by a machine.

7. The method of claim 1, wherein the control is a baseline signal intensity.

8. The method of claim 7, wherein the baseline signal intensity is obtained prior to or at the start of the breathing maneuver.

9. The method of claim 2, wherein the control comprises at least one of measured oxygenation or blood flow in a healthy tissue within the image and a measured oxygenation or blood flow in a stored image of a reference tissue.

10. The method of claim 9, wherein the reference tissue is at least one of healthy myocardium and a skeletal muscle.

11. The method of claim 1, wherein the oxygenation is measured using an oxygen sensitive imaging technique.

12. The method of claim 11, wherein the oxygen sensitive imaging technique comprises blood oxygen level dependent magnetic resonance imaging (BOLD-MRI), nuclear techniques, single-photon emission computed tomography/SPECT, positron emission tomography/PET, computed tomography/CT, echocardiography or other ultrasound, near infrared spectroscopy/NIRS, intravascular blood flow measurements, fractional flow reserve, impedance measurements of the myocardium or other organ, or a combination thereof.

13. The method of claim 1, wherein the heart function comprises microvascular or macrovascular function.

14. The method of claim 1, wherein the reduced heart function comprises heart disease.

15. The method of claim 14, wherein the heart disease comprises ischemic heart disease, coronary heart disease, heart disease caused by arterial hypertension, diabetes mellitus, hypercholesterolemia, obesity, non-ischemic cardiomyopathies, or myocardial inflammation, congenital heart disease, valvular heart disease, stress-induced cardiomyopathy, microvascular dysfunction or coronary artery stenosis.

16. The method of claim 1, wherein the method does not include infusion of a vasodilator in the subject.

17. The method of claim 1, wherein the abnormal response comprises a blunted increase compared to the control, a lack of increase compared to the control, a decrease compared to the control or an increase compared to the control.

18. A system for diagnosing heart function or other organ function comprising:
   an imaging device; and
   a processor configured to assess heart function or other organ function according to the method of claim 1.

19. A method of assessing microvascular or macrovascular function in a subject comprising:
   measuring a change in at least one of oxygenation and blood flow in an organ of the subject in response to at least one breathing maneuver;
   comparing the change in at least one of measured oxygenation and blood flow to a control; and
   assessing microvascular or macrovascular function in accordance with the comparison result, wherein an abnormal response in at least one of oxygenation and blood flow in the organ compared to the control is indicative of reduced microvascular or macrovascular function.

20. The method of claim 19, wherein:
   measuring the change comprises:
   imaging the organ while oxygenation of the organ is altered in response to the at least one breathing maneuver, to produce an image,
   segmenting the image, and
   determining a signal intensity of a region of interest in a segment of the image;
   comparing the change comprises comparing the signal intensity to a control; and
   assessing function comprises assessing microvascular or macrovascular function in accordance with the comparison result, wherein an abnormal change in the signal intensity is indicative of reduced microvascular or macrovascular function.

21. A system for assessing microvascular or macrovascular function comprising an imaging device and a processor configured to assess microvascular or macrovascular function according to the method of claim 19.

* * * * *